(12) United States Patent
Iida et al.

(10) Patent No.: US 10,150,220 B2
(45) Date of Patent: Dec. 11, 2018

(54) MANIPULATOR CONTROL METHOD, MANIPULATOR, AND MANIPULATOR SYSTEM

(71) Applicant: OLYMPUS CORPORATION, Tokyo (JP)

(72) Inventors: Masatoshi Iida, Tokyo (JP); Ryuichi Yorimoto, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 76 days.

(21) Appl. No.: 15/368,834

(22) Filed: Dec. 5, 2016

(65) Prior Publication Data

US 2017/0080581 A1 Mar. 23, 2017

Related U.S. Application Data

(63) Continuation of application No. PCT/JP2015/064911, filed on May 25, 2015.

(30) Foreign Application Priority Data

Jun. 19, 2014 (JP) .................................. 2014-126371

(51) Int. Cl.
*G05B 15/00* (2006.01)
*G05B 19/00* (2006.01)
(Continued)

(52) U.S. Cl.
CPC ............... *B25J 18/06* (2013.01); *A61B 34/37* (2016.02); *A61B 34/71* (2016.02); *A61B 90/00* (2016.02);
(Continued)

(58) Field of Classification Search
None
See application file for complete search history.

(56) References Cited

U.S. PATENT DOCUMENTS

2008/0059131 A1* 3/2008 Tokita ..................... G06F 3/011
                                                                 703/5
2009/0112060 A1    4/2009 Sugiyama et al.
(Continued)

FOREIGN PATENT DOCUMENTS

JP    2000-279376 A    10/2000
JP    2008-289556 A    12/2008
(Continued)

OTHER PUBLICATIONS

Japanese Office Action dated Jun. 6, 2017 in Japanese Patent Application No. 2014-126371.
(Continued)

*Primary Examiner* — Bhavesh V Amin
(74) *Attorney, Agent, or Firm* — Scully, Scott, Murphy & Presser, P.C.

(57) ABSTRACT

A method for controlling a manipulator includes a joint structure portion having one or more joints connected to a distal end of an insertion portion, a power transmission member inserted into the insertion portion to transmit driving force to the joint structure portion, and a driving portion that drives the power transmission member and which is guided to an application site by being inserted into the channel member. When the manipulator is operated in an insertion control mode for inserting the joint structure portion into the channel member, the method includes detecting a load amount generated in the power transmission member or the driving portion; and creating a bending state in which the joint structure portion follows the channel member by controlling a driving amount of the power transmission member by the driving portion such that the load amount becomes within a predetermined target control range.

17 Claims, 18 Drawing Sheets

(51) Int. Cl.
  *G06F 19/00* (2018.01)
  *B25J 18/06* (2006.01)
  *A61B 90/00* (2016.01)
  *A61B 34/37* (2016.01)
  *A61B 34/00* (2016.01)
  *B25J 13/08* (2006.01)
  *B25J 9/10* (2006.01)
  *B25J 9/16* (2006.01)
  *A61B 34/30* (2016.01)

(52) U.S. Cl.
  CPC .......... *B25J 9/1045* (2013.01); *B25J 9/1689* (2013.01); *B25J 13/085* (2013.01); *A61B 2034/301* (2016.02); *A61B 2034/715* (2016.02); *A61B 2090/064* (2016.02)

(56) References Cited

U.S. PATENT DOCUMENTS

| | | | |
|---|---|---|---|
| 2009/0112316 A1 | 4/2009 | Umemoto et al. | |
| 2010/0042077 A1 | 2/2010 | Okada | |
| 2011/0295247 A1 | 12/2011 | Schlesinger et al. | |
| 2012/0046522 A1 | 2/2012 | Naito | |
| 2013/0089392 A1* | 4/2013 | Iida | F16C 1/26 414/7 |
| 2013/0310977 A1* | 11/2013 | Tsusaka | B25J 9/1656 700/257 |
| 2016/0207196 A1* | 7/2016 | Ohnishi | B25J 3/04 |
| 2017/0080581 A1* | 3/2017 | Iida | B25J 18/06 |

FOREIGN PATENT DOCUMENTS

| | | |
|---|---|---|
| JP | 2009-101077 A | 5/2009 |
| JP | 2009-107074 A | 5/2009 |
| JP | 2009-537232 A | 10/2009 |
| JP | 2009-539573 A | 11/2009 |
| JP | 2010-035768 A | 2/2010 |
| JP | 2012-527948 A | 11/2012 |
| JP | 2014-512863 A | 5/2014 |
| WO | WO 2007/136803 A2 | 11/2007 |
| WO | 2007/146987 A1 | 12/2007 |
| WO | 2009/120982 A2 | 10/2009 |
| WO | 2010/138083 A1 | 12/2010 |
| WO | WO 2012/112274 A1 | 8/2012 |

OTHER PUBLICATIONS

International Search Report dated Aug. 4, 2015 issued in PCT/JP2015/064911.

Extended Supplementary European Search Report dated Jan. 2, 2018 in European Patent Application No. 15 81 0165.9.

* cited by examiner

MANIPULATOR CONTROL METHOD, MANIPULATOR, AND MANIPULATOR SYSTEM

This application is a continuation application based on a PCT International Application No. PCT/JP2015/064911, filed on May 25, 2015, whose priority is claimed on Japanese Patent Application No. 2014-126371, filed on Jun. 19, 2014. The contents of both the PCT International Application and the Japanese Patent Application are incorporated herein by reference.

BACKGROUND OF THE INVENTION

Field of the Invention

The present invention relates to a manipulator control method, a manipulator, and a manipulator system.

Description of Related Art

Conventionally, a manipulator having a joint structure portion provided at a distal end thereof to perform various treatments inside of a human body, a device, or the like, for example, is known.

Such a manipulator is introduced into a portion of a treatment target by being inserted into an insertion channel of a tubular member that extends into the treatment target. Due to this, the joint structure portion of the manipulator is provided at a distal end of a flexible insertion portion to be inserted into the channel even when the channel is bent, and the joint structure portion is driven by a manipulating portion in a proximal end of the insertion portion.

Japanese Unexamined Patent Application, First Publication No. 2009-101077 discloses a medical device including a treatment tool which is an example of such a manipulator.

This treatment tool includes an insertion portion having a distal bending portion which is bent in an arbitrary direction by the driving force of a driving portion. This treatment tool is used by being inserted into a treatment tool channel of an endoscope device of which the distal end is disposed near a treatment site (an application site).

The distal bending portion is configured of three bending pieces disposed in series that are rotatably connected in two axial directions by two joints.

SUMMARY OF THE INVENTION

According to a first aspect of the present invention, a manipulator control method for controlling a manipulator which includes a joint structure portion having one or more joints connected to a distal end of an insertion portion, a power transmission member inserted into the insertion portion to transmit driving force to the joint structure portion, and a driving portion that drives the power transmission member, and which is guided to an application site by being inserted into a channel member, wherein when the manipulator is operated in an insertion control mode used for inserting the joint structure portion into the channel member, the manipulator control method includes: detecting a load amount generated in the power transmission member or the driving portion; and creating a bending state in which the joint structure portion follows the channel member by controlling a driving amount of the power transmission member by the driving portion such that the load amount becomes within a predetermined target control range.

According to a second aspect of the present invention, in the manipulator control method according to the first aspect, the load amount may be a tension generated in the power transmission member.

According to a third aspect of the present invention, in the manipulator control method according to the first or second aspect, the manipulator control method may further include: detecting the load amount while bending the joint by supplying an operation command value for allowing the joint to perform a bending operation periodically to the driving portion; and performing control to change the operation command value such that a maximum value and a minimum value of the load amount become within the target control range.

According to a fourth aspect of the present invention, in the manipulator control method according to the third aspect, in a case where the joint structure portion has a plurality of the joints, when the operation command value is going to be supplied to a control target joint of the joint structure portion, the manipulator control method may further include: detecting a bending state of the other joint of the joint structure portion; and supplying the operation command value which involves correction for removing influence of mutual interference caused by the other joint based on the bending state of the other joint.

According to a fifth aspect of the present invention, in the manipulator control method according to the second aspect, the power transmission member may have a first transmission portion that bends the joint in a first direction and a second transmission portion that bends the joint in a second direction opposite to the first direction, the driving portion may have a first driving portion that drives the first transmission portion and a second driving portion that drives the second transmission portion, and the manipulator control method may further include: detecting tensions generated in the first and second transmission portions; and performing control to drive the first and second transmission portions by independently driving the first and second driving portions such that both of the tensions are equal to a predetermined initial insertion tension.

According to a sixth aspect of the present invention, in the manipulator control method according to the second aspect, the power transmission member may have a first transmission portion that bends the joint structure portion in a first direction and a second transmission portion that bends the joint structure portion in a second direction opposite to the first direction, and the manipulator control method may further include: detecting tensions generated in the first and second transmission portions to acquire information of a tension difference between these tensions; and performing control to drive the power transmission member to cause the tension difference to be 0.

According to a seventh aspect of the present invention, in the manipulator control method according to the fifth or sixth aspect, an initial tension of the power transmission member may be set to be lower than an initial tension of the power transmission member when the manipulator is used at the application site.

According to an eighth aspect of the present invention, a manipulator which is guided to an application site by being inserted into a channel member, includes a joint structure portion having one or more joints connected to a distal end of an insertion portion; a power transmission member inserted into the insertion portion to transmit driving force to the joint structure portion; a driving portion that is configured to drive the power transmission member; a load amount detection portion that is configured to detect a load amount generated in the power transmission member or the driving portion; and an operation control portion that is configured to control an operation of the joint structure portion, wherein the operation control portion sets an insertion control mode for inserting the joint structure portion into the channel member, and wherein the operation control portion controls a driving amount of the power transmission member by the driving portion such that the load amount detected by the load amount detection portion becomes within a predetermined target control range to create a bending state in which the joint structure portion follows the channel member, when the operation control portion is set to the insertion control mode.

According to a ninth aspect of the present invention, in the manipulator according to the eighth aspect, the load amount detection portion may detect a tension generated in the power transmission member as the load amount.

According to a tenth aspect of the present invention, in the manipulator according to the eighth or ninth aspect, the operation control portion may detect the load amount while bending the joint by supplying an operation command value to the driving portion for allowing the joint to perform a bending operation periodically, and the operation control portion may perform control to change the operation command value such that a maximum value and a minimum value of the load amount become within the target control range.

According to an eleventh aspect of the present invention, in the manipulator according to the tenth aspect, the joint structure portion may have a plurality of joints, the operation control portion may detect a bending state of the other joint of the joint structure portion, and the operation control portion may supply the operation command value which involves correction for removing influence of mutual interference caused by the other joint based on the bending state of the other joint, when the operation command value is going to be supplied to a control target joint of the joint structure portion.

According to a twelfth aspect of the present invention, in the manipulator according to the ninth aspect, the power transmission member may have a first transmission portion that bends the joint in a first direction and a second transmission portion that bends the joint in a second direction opposite to the first direction, the driving portion may have a first driving portion that drives the first transmission portion and a second driving portion that drives the second transmission portion, the load amount detection portion may have a first detection portion that detects the tension of the first transmission portion and a second detection portion that detects the tension of the second transmission portion, and the operation control portion may perform control to drive the first and second transmission portions by independently driving the first and second driving portions such that the tensions detected by the first and second detection portions are equal to a predetermined initial insertion tension.

According to a thirteenth aspect of the present invention, in the manipulator according to the ninth aspect, the power transmission member may have a first transmission portion that bends the joint in a first direction and a second transmission portion that bends the joint in a second direction opposite to the first direction, the load amount detection portion may have a first detection portion that detects the tension of the first transmission portion and a second detection portion that detects the tension of the second transmission portion, and the operation control portion may acquire information on a tension difference between the tension detected by the first detection portion and the tension detected by the second detection portion; and the operation control portion may perform control to drive the power transmission member to cause the tension difference to reach 0.

According to a fourteenth aspect of the present invention, in the manipulator according to the twelfth or thirteenth aspect, an initial tension of the power transmission member may be set to be lower than an initial tension of the power transmission member when the manipulator is used at the application site.

According to a fifteenth aspect of the present invention, a manipulator system includes the manipulator according to any one of the eighth to thirteenth aspects.

DETAILED DESCRIPTION OF THE INVENTION

Figure 1:
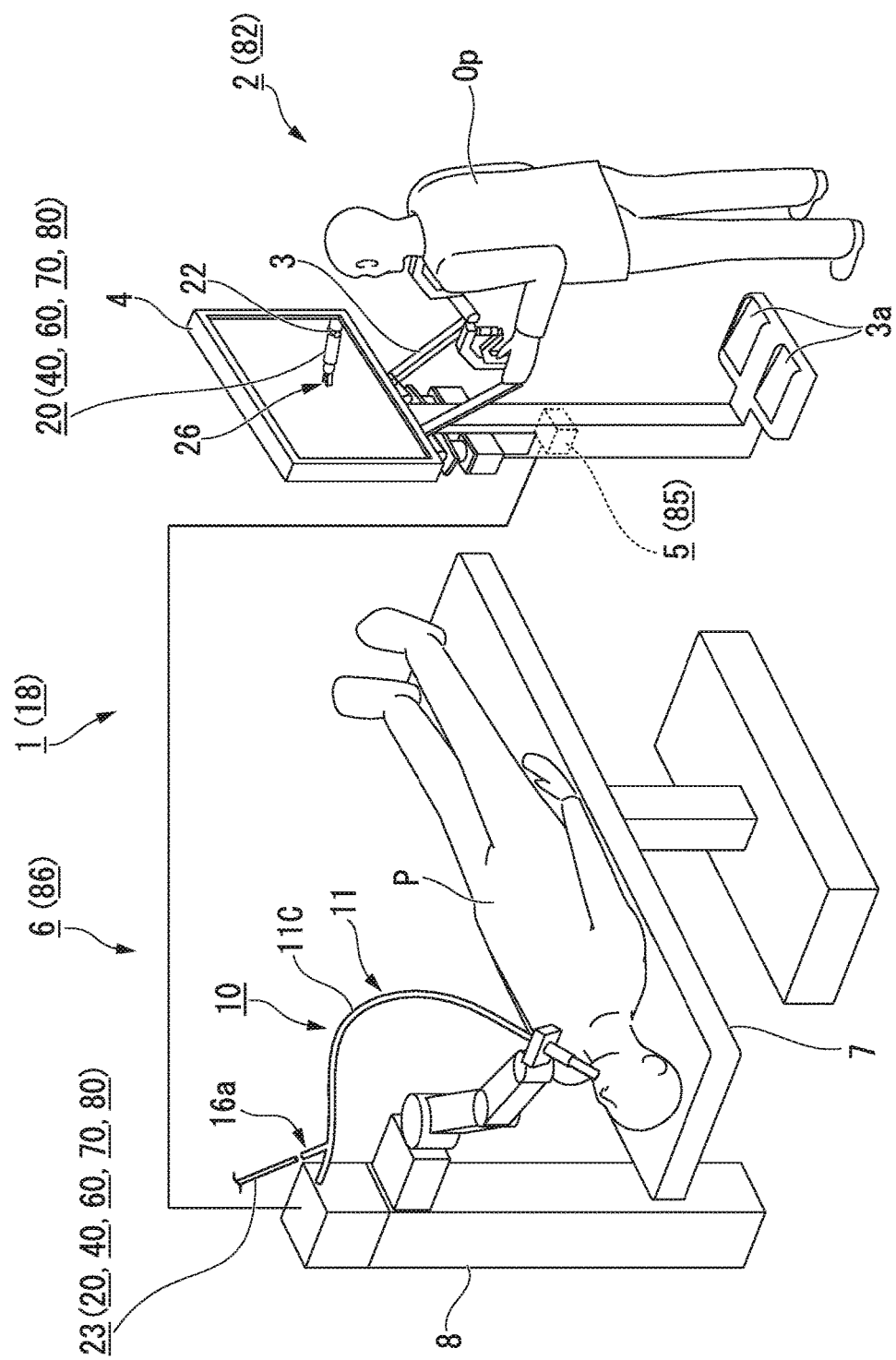
FIG. 1 is a schematic perspective view showing an entire configuration of a manipulator system according to a first embodiment of the present invention.

Hereinafter, embodiments of the present invention will be described with reference to the accompanying drawings. In all drawings, the same or corresponding members in different embodiments are denoted by the same reference numerals, and a redundant description thereof will not be provided.
[First Embodiment]
A manipulator and a manipulator system according to a first embodiment of the present invention will be described.

Figure 2:
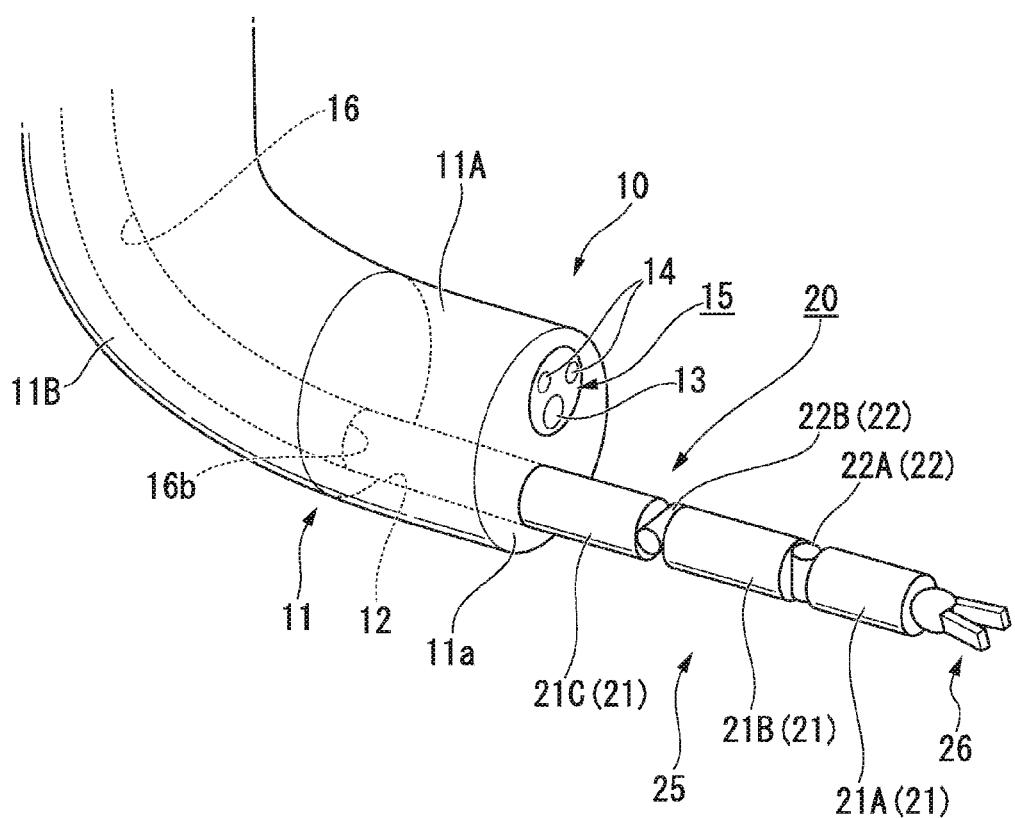
FIG. 2 is a schematic perspective view showing an appearance of a distal end of a manipulator according to the first embodiment of the present invention.
Figure 3A:
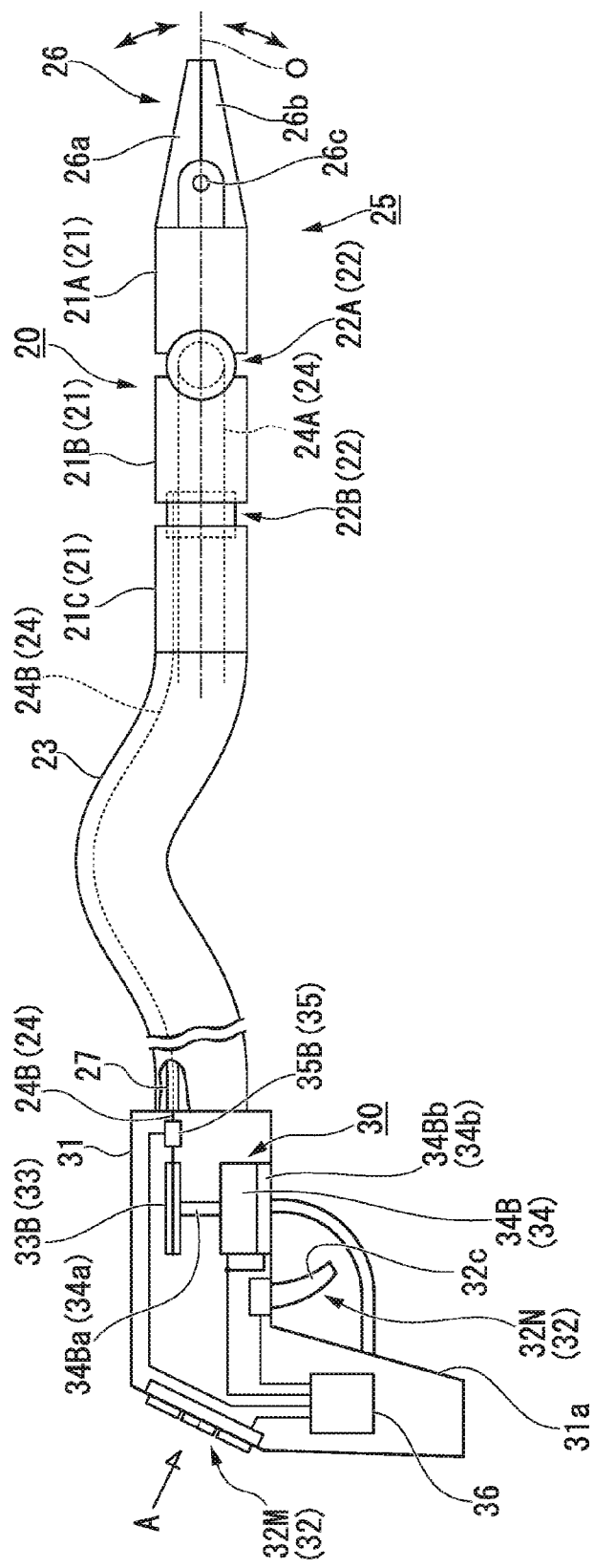
FIG. 3A is schematic diagram showing a configuration of the manipulator according to the first embodiment of the present invention.
Figure 3B:
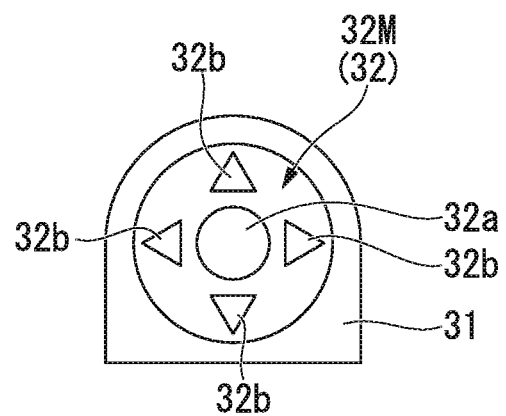
FIG. 3B is a schematic diagram taken along arrow A, showing a configuration of the manipulator according to the first embodiment of the present invention.
Figure 4:
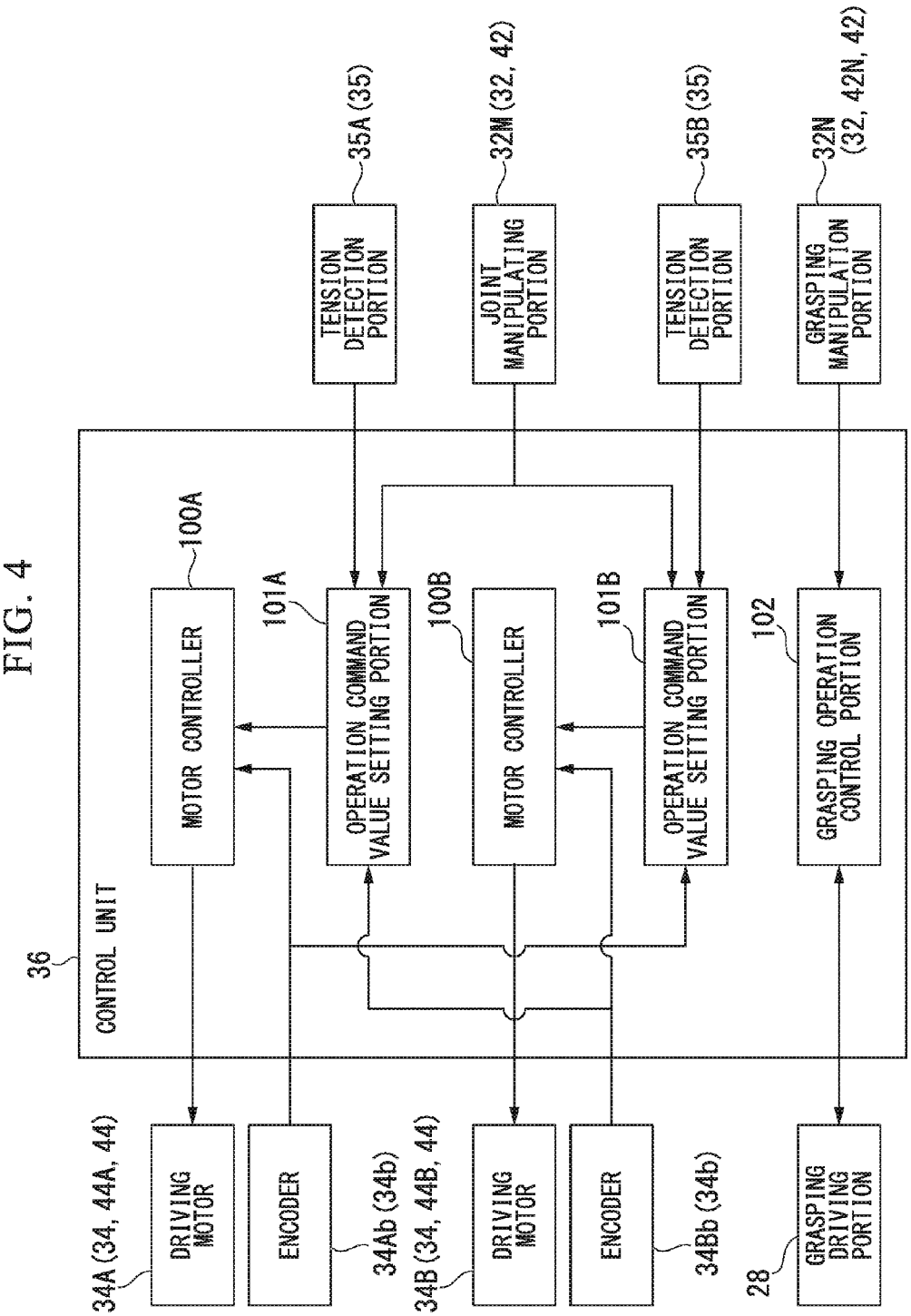
FIG. 4 is a functional block diagram showing a functional configuration of a control unit of the manipulator according to the first embodiment of the present invention.

FIG. 1 is a schematic perspective view showing an entire configuration of a manipulator system according to a first embodiment of the present invention. FIG. 2 is a schematic perspective view showing an appearance of a distal end of a manipulator according to the first embodiment of the present invention. FIG. 3A is schematic diagram showing a configuration of the manipulator according to the first embodiment of the present invention. FIG. 3B is a diagram taken along arrow A in FIG. 3A. FIG. 4 is a functional block diagram showing a functional configuration of a control unit of the manipulator according to the first embodiment of the present invention.

Since the drawings are schematic diagrams, the dimensions and the shapes are appropriately different (the same is true for the subsequent drawings).

As shown in FIG. 1, a manipulator system 1 according to the present embodiment is a so-called master slave system including a master manipulator 2 which is manipulated by an operator Op and a slave manipulator 6 in which a treatment endoscope device 10 for guiding a medical device 20 (a manipulator) to the vicinity of a treatment site is provided.

The master manipulator 2 includes a master arm 3 with which the operator Op inputs a manipulation, a display unit 4 that displays a video or the like captured using the treatment endoscope device 10, and a control unit 5 that generates a manipulation command for operating the slave manipulator 6 based on the operation of the master arm 3.

The master arm 3 is a manipulating portion for operating respective portions of the slave manipulator 6. Although the details are not depicted, the master manipulator 2 includes a pair of master arms 3 corresponding to the right and left hands of the operator Op.

The master arm 3 has a joint structure for operating a manipulator having a joint having at least one degree of freedom like a bending portion 11B (see FIG. 2) of the treatment endoscope device 10 which will be described later, for example.

Moreover, when a grasping portion is provided at a distal end of the treatment endoscope device 10, for example, a grasping manipulation portion (not shown) capable of manipulating the grasping portion is provided at an end of the master arm 3 positioned close to the operator Op.

The display unit 4 is a device on which the video of a treatment target portion captured by an observation unit 15 (see FIG. 2) attached to the treatment endoscope device 10 (described later), a manipulation screen necessary for manipulations, information supplied from the control unit 5, and the like are displayed. When the medical device 20 is inserted into the treatment endoscope device 10, the medical device 20 is also displayed on the display unit 4 together with the treatment target portion as shown in FIG. 1.

Another manipulating portion to which an appropriate manipulation function is allocated is also provided in the master manipulator 2. Examples of such a manipulating portion include a manipulation switch (not shown) including buttons, levers, and the like, a foot switch 3a, and the like.

The slave manipulator 6 includes a table 7 on which a patient P is placed and a multi-joint robot 8 disposed near the table 7.

The treatment endoscope device 10 is held on the multi-joint robot 8. The medical device 20 can be inserted into the treatment endoscope device 10.

The multi-joint robot 8 and the treatment endoscope device 10 operate according to a manipulation command supplied from the master manipulator 2.

In the manipulator system of the present invention, the multi-joint robot 8 is not essential, and an assistant (not shown) may hold the treatment endoscope device 10, for example.

As shown in FIG. 2, the treatment endoscope device 10 has a sheath tube 11 which is an elongated member for being inserted into the body of the patient P.

The sheath tube 11 includes a tubular insertion portion 11C (see FIG. 1) having flexibility, a known bending portion 11B having a joint ring, a bending piece, and the like, for example, and a circular columnar distal end 11A formed of a rigid material, which are arranged in that order from a proximal end to a distal end.

The bending portion 11B can change the direction of the distal end 11A by being bent according to a manipulation input to the master arm 3. As an example of a mechanism for bending the bending portion 11B, a known configuration in which a driving wire inserted into an inner circumferential surface of a joint ring or a bending piece and fixed to the distal end 11A is inserted into the insertion portion 11C and is pulled by a driving motor or the like disposed close to the proximal end may be employed.

A treatment tool channel 16 (a channel member) which is a path along which a treatment tool such as the medical device 20 is guided to the vicinity of a treatment site is provided inside the insertion portion 11C and the bending portion 11B.

As shown in FIG. 1, a supply opening 16a (an insertion opening) that is open to a lateral side of the insertion portion 11C is connected to the proximal end (the proximal side) of the treatment tool channel 16.

The treatment tool channel 16 is formed of a flexible tubular member having such an inner diameter that at least the medical device 20 can be inserted therein. As shown in FIG. 2, a distal end 16b of the treatment tool channel 16 is connected to a proximal side of a through-hole 12 that passes through the distal end 11A in an axial direction and is open to a distal end surface 11a of the distal end 11A.

As shown in FIG. 2, the observation unit 15 is a device for observing a treatment target portion and includes a known imaging mechanism 13 and a known illumination mechanism 14.

The imaging mechanism 13 and the illumination mechanism 14 are disposed inside the distal end 11A, and electrical wires and optical fibers which are not shown are inserted into the bending portion 11B and the insertion portion 11C and are connected to an electric circuit and a light source of the control unit 5.

The imaging mechanism 13 and the illumination mechanism 14 have optical opening windows formed in the distal end surface 11a of the distal end 11A and can receive external light on the front side of the distal end 11A and emit illumination light to the front side through the opening windows.

The medical device 20 is an example of a manipulator which includes a joint structure portion having a plurality of joints to move and drive an end effector at a distal end thereof and is formed in a generally elongated shaft form.

As shown in FIG. 3A, the medical device 20 includes a joint 22, a shaft-shaped portion 21 connected to the joint 22, a grasping portion 26 that grasps a treatment target or the like, a tubular portion 23 (an insertion portion) which is a flexible tubular member, a driving unit 30 that supplies driving force to the joint 22 and the grasping portion 26, a manipulating portion 32 that manipulates the joint 22 and the grasping portion 26, and a control unit 36 (an operation control portion) that controls the operation of the driving unit 30 based on a manipulation of the manipulating portion 32.

The grasping portion 26 is an end effector of the medical device 20 and is attached to a distal end of the shaft-shaped portion 21 on the most distal end side (distal side).

The tubular portion 23 is connected to the shaft-shaped portion 21 on the most proximal end side (proximal side).

The joint 22 is a bending joint and a specific configuration thereof is not particularly limited as long as the joint performs bending by transmitting driving force from a proximal end using a power transmission member. The degree of bending freedom, the bending direction, the amount of bending, and the like of the joint 22 are not particularly limited.

In the following description, as an example of the joint 22, a configuration which includes a joint 22B that bends in a direction crossing an extension direction of the medical device 20 and a joint 22A that bends in a direction orthogonal to the bending direction of the joint 22B and in which the joints 22B and 22A are arranged in that order from the proximal side will be described.

The joints 22A and 22B have pulleys (not shown), and driving wires 24A and 24B which are power transmission members that transmit driving force to the joints 22A and 22B are wound around the respective pulleys and the ends of the driving wires are fixed to the pulleys.

In the following description, when the joints 22A and 22B or the driving wires 24A and 24B are not particularly distinguished or are collectively mentioned, the letters A and B are omitted and they are sometimes simply referred to as the joint 22 and the driving wire 24.

Moreover, in the present specification, for the sake of simplicity, members or portions which are definitely related to the joints 22A and 22B or the driving wires 24A and 24B are denoted by reference numerals with the letters A and B when it is necessary to express their correlation. These members or portions have approximately the same configuration (including a case in which they have exactly the same configuration) unless particularly stated otherwise. Furthermore, when it is not necessary to distinguish those members or portions or they are collectively mentioned, the letters A and B are omitted.

The shaft-shaped portion 21 includes shaft-shaped portions 21C and 21B connected by the joint 22B and a shaft-shaped portion 21A connected to the shaft-shaped portion 21B by the joint 22A.

Due to this, the shaft-shaped portion 21C is a portion of the shaft-shaped portion 21 located closest to the proximal end of the medical device 20, and an end of the shaft-shaped portion 21C opposite the end to which the joint 22B is connected is fixed to the distal end of the tubular portion 23.

The shaft-shaped portion 21A is the shaft-shaped portion 21 located closest to the distal end of the medical device 20, and the grasping portion 26 is fixed to its distal end which is an end opposite the joint 22A.

The joints 22B and 22A are connected to both ends of the shaft-shaped portion 21B.

A connector including the shaft-shaped portion 21C, the joint 22B, the shaft-shaped portion 21B, the joint 22A, the shaft-shaped portion 21A, and the grasping portion 26 is referred to as a distal bending portion 25 (a joint structure portion).

The shaft-shaped portions 21A, 21B, and 21C have an outer diameter smaller than the inner diameter of the treatment tool channel 16 and the through-hole 12 of the distal end 11A.

The joints 22 are formed in a size at which they do not protrude further than the outer shape of the connected shaft-shaped portion 21.

The length of each of the shaft-shaped portions 21A, 21B, and 21C is set such that, when the treatment tool channel 16 is bent in a minimum allowable radius of bend, a bending state in which the distal bending portion 25 can be inserted into the treatment tool channel 16 by appropriately rotating the joints 22 is created.

The grasping portion 26 includes a pair of grasping members 26a and 26b for holding a treatment tool, a tissue, and the like, for example, and a rotating shaft 26c that rotatably supports the grasping members 26a and 26b. When a grasping manipulation portion 32N is manipulated, the grasping members 26a and 26b are rotated about the rotating shaft 26c and are opened and closed by moving along arrows as indicated in FIG. 3A.

Means for transmitting the driving force of the grasping portion 26 are not particularly limited, and for example, means for driving links (not shown) connected to the grasping members 26a and 26b by a driving wire (not shown) may be used. In the following description, it is assumed that the grasping portion 26 is driven by a driving wire like the driving wire 24 as an example.

As shown in FIG. 3A, the grasping portion 26 has a size at which it does not protrude further than the outer shape of the connected shaft-shaped portion 21 when the grasping portion 26 is closed without grasping any object.

Due to this, in a state in which the distal bending portion 25 extends straight and covers the grasping portion 26 as described above, the distal bending portion 25 is a shaft-shaped body that can be inserted to be able to advance toward and retract from the through-hole 12.

The tubular portion 23 is formed of a flexible tubular member such as a resin tube, for example, and an object such as the driving wires 24A and 24B is inserted therein.

The driving wires 24A and 24B are inserted into sheaths 27 of which the positions of both ends are fixed, in a space from the proximal end of the tubular portion 23 to a position near the pulley at the distal end.

Each sheath 27 is formed of a densely wound coil or the like having approximately the same inner diameter as the dimension of each driving wire 24. Due to this, the length of the sheath 27 does not easily change even when the sheath 27 is bent by receiving external force.

Examples of an object other than the driving wire 24 that is inserted into the tubular portion 23 include a manipulation wire for driving the grasping portion 26 and an electrical wire, an optical fiber, or the like connected to the observation unit 15, but these examples are not shown in the drawings.

The driving unit 30, the manipulating portion 32, and the control unit 36 are provided inside or on the surface of a proximal housing 31 having a grip portion 31a which is fixed to the proximal end of the tubular portion 23 and can be grasped by the hand of the operator Op.

The driving unit 30 is a device portion that drives the driving wire 24 to supply driving force to the joint 22 and drives a driving wire (not shown) to supply driving force to the grasping portion 26.

The driving unit 30 includes a plurality of driving motors 34 (driving portions) fixed to the proximal housing 31 and provided in respective driving wires 24 for driving the joint 22 and a grasping driving portion 28 (not shown in FIG. 3A, see FIG. 4) for driving the grasping portion 26.

In the following description, when the driving motor 34 is configured to drive the joint 22A (22B), the driving motor 34 will be referred to as a driving motor 34A (34B).

FIG. 3A shows the driving motor 34B that drives the driving wire 24B as an example among the driving portions of the driving unit 30.

An output shaft 34Ba of the driving motor 34B is connected to a driving pulley 33B around which the driving wire 24B is wound. When the driving motor 34B is rotated, the driving pulley 33B rotates and thus the driving wire 24B can be pulled in a rotating direction.

The type of the driving motor 34B is not particularly limited as long as the driving motor 34B can rotate the output shaft 34Ba by a predetermined amount based on a manipulation command value. For example, a servo motor, a step motor, a DC motor, and the like can be employed.

In the present embodiment, the driving motor 34B has an encoder 34Bb that detects a rotation position of the output shaft 34Ba and is communicably connected to the control unit 36 that controls driving of the driving motor 34B based on a manipulation of the manipulating portion 32.

While the driving motor 34B for driving the driving wire 24B and members related thereto have been described with reference to FIG. 3A, the same description also applies to a driving motor 34A, an output shaft 34Aa, a driving pulley 33A, and an encoder 34Ab, which are not shown in FIG. 3A.

Moreover, the same driving motor as the driving motor 34 can be employed as the grasping driving portion 28 although a control method is different.

Moreover, the driving unit 30 according to the present embodiment includes a tension detection portion 35 that detects a load amount as tension as a load amount detection portion that detects a load amount generated in each driving wire 24.

A configuration of the tension detection portion 35 is not particularly limited as long as it can detect tension, and for example, a configuration which uses a strain gauge can be employed.

In the present embodiment, a load cell attached to the driving wire 24 inserted into the proximal housing 31 is employed as an example of the tension detection portion 35.

The tension detection portion 35 is communicably connected to the control unit 36.

In the following description, when the tension detection portion 35 is configured to detect tension generated in the driving wire 24A (24B), the tension detection portion 35 is referred to as a tension detection portion 35A (35B).

As shown in FIG. 3A, the manipulating portion 32 includes a joint manipulating portion 32M that inputs manipulations related to the operation of the joint 22 and a grasping manipulation portion 32N that inputs manipulations related to the operation of the grasping portion 26.

As shown in FIG. 3B, the joint manipulating portion 32M includes a mode switch 32a and a bending manipulation button 32b and is communicably connected to the control unit 36.

The mode switch 32a is a switch that switches a control mode of the joint 22 between an "insertion control mode" and an "operation control mode," and for example, a press button switch, a slide switch, a toggle switch, and the like can be employed.

A control mode which is set can be identified based on a manipulation state of the switch, a light emission state, or the like, for example.

Here, the "insertion control mode" is a control mode which is recommended to be selected when performing an insertion operation of inserting the medical device 20 into the treatment tool channel 16 and removing the same from the treatment tool channel 16.

In this control mode, manipulation of the bending manipulation button 32b is disabled, and an operation in which each joint 22 is automatically controlled by the control unit 36 (described later) is allowed.

Moreover, in this control mode, manipulation of the grasping manipulation portion 32N is disabled such that the grasping portion 26 does not open during insertion of the medical device 20.

Moreover, the "operation control mode" is a control mode in which the operator Op can manipulate the distal bending portion 25 using the bending manipulation button 32b and is a control mode suggested in cases other than when inserting the medical device 20 into the treatment tool channel 16.

In this control mode, manipulation of the bending manipulation button 32b and manipulation of the grasping manipulation portion 32N are enabled.

In the present embodiment, the bending manipulation button 32b is provided at each of the four positions about the center of the mode switch 32a at which the circumference is evenly divided.

A first pair of the bending manipulation buttons 32b facing each other with the mode switch 32a interposed therebetween are disposed in a longitudinal direction of the grip portion 31a to manipulate the rotation of the joint 22A and a second pair of the bending manipulation buttons 32b are disposed in a direction orthogonal to the first pair to manipulate the rotation of the joint 22B.

Due to this, the arrangement of the bending manipulation buttons 32b indicates a bending direction in which the distal bending portion 25 is bent about a central axial line O (see FIG. 3A) of the medical device 20.

Rotation amounts of the joints 22A and 22B corresponding to an amount of bend in each bending direction are set by detecting a period in which the bending manipulation buttons 32b are pressed.

In the operation control mode, when pressing of the bending manipulation button 32b is detected, the position of the pressed bending manipulation button 32b and the pressing period are detected. In this way, manipulation information for the rotation amount of the joint 22A or 22B is generated from the information on the pressed bending manipulation button 32b and the pressing period and the manipulation information is transmitted to the control unit 36.

The grasping manipulation portion 32N is a manipulating portion for performing an opening/closing manipulation of the grasping portion 26 which is a treatment tool portion of the medical device 20. In the present embodiment, as shown in FIG. 3A, the grasping manipulation portion 32N includes a manipulation lever 32c and is communicably connected to the control unit 36.

A movement position of the manipulation lever 32c is correlated with an opening angle of the grasping portion 26. When the operator Op manipulates the manipulation lever 32c, a movement amount of the manipulation lever 32c of the grasping manipulation portion 32N is detected and an opening amount of the grasping portion 26 is set according to the movement amount.

Information on the opening amount of the grasping portion 26 is transmitted to the control unit 36.

Next, a functional configuration of the control unit 36 will be described.

As shown in FIG. 4, the control unit 36 includes operation command value setting portions 101A and 101B, motor controllers 100A and 100B, and a grasping operation control portion 102.

The operation command value setting portion 101A (101B) is configured to set an operation command value of the driving motor 34A (34B) based on the manipulation information of the joint 22A (22B) transmitted from the joint manipulating portion 32M.

However, the operation command value setting portion 101A performs control of changing the manipulation information transmitted from the joint manipulating portion 32M as necessary based on the information on the tension of the driving wire 24A transmitted from the tension detection portion 35A and information on the present rotation positions of the driving motors 34A and 34B transmitted from the encoders 34Ab and 34Bb.

Moreover, the operation command value setting portion 101B performs control of changing the manipulation information transmitted from the joint manipulating portion 32M as necessary based on the information on the tension of the driving wire 24B transmitted from the tension detection portion 35B and information on the present rotation positions of the driving motors 34A and 34B transmitted from the encoders 34Ab and 34Bb.

The details of the control of changing these items of manipulation information will be described later together with description of operations.

The motor controller 100A (100B) is configured to control the rotation amount of the driving motor 34A (34B) based on the operation command value transmitted from the operation command value setting portion 101A (101B).

The grasping operation control portion 102 is configured to control the operation of the grasping driving portion 28 that drives the grasping portion 26 based on the operation command value transmitted from the grasping manipulation portion 32N.

Such a control unit 36 is configured as a computer including a CPU, a memory, an input and output interface, an external storage device, and the like, and an appropriate control program that realizes the above-described control function is executed by the control unit 36.

Next, the operation of the medical device 20 of the manipulator system 1 will be described with focus on a manipulator control method according to the present embodiment.

Figure 5:
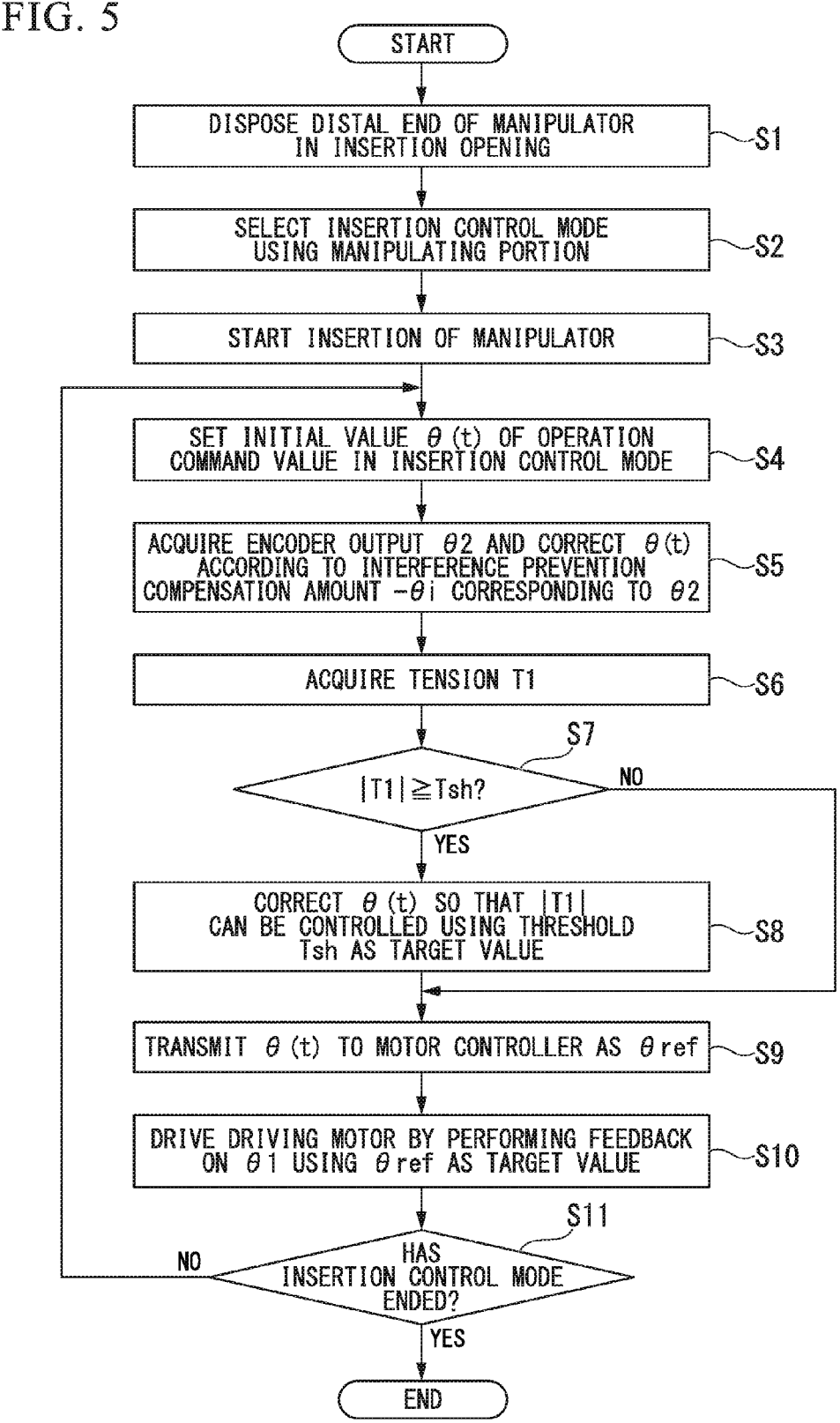
FIG. 5 is a flowchart showing the flow of a manipulator control method according to the first embodiment of the present invention.
Figure 6:
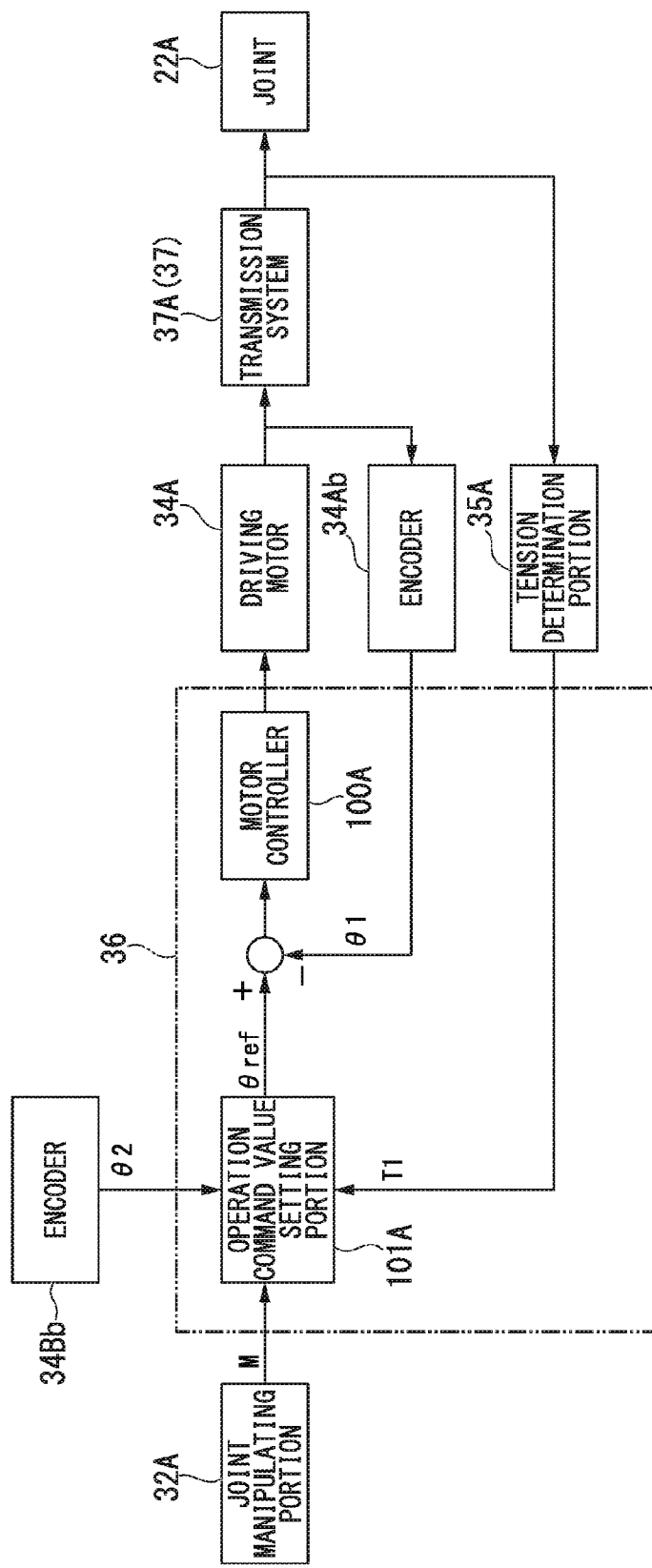
FIG. 6 is a control block diagram of the manipulator according to the first embodiment of the present invention.
Figure 7A:
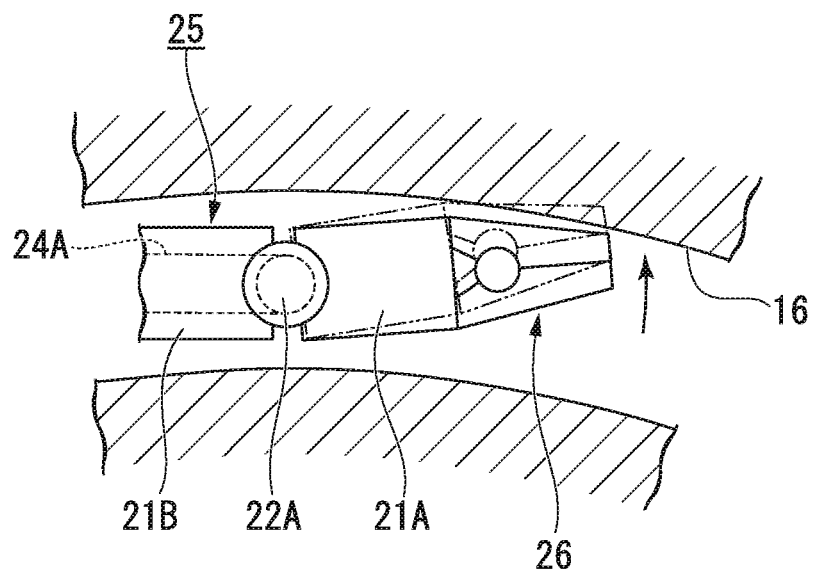
FIG. 7A is a diagram showing operations when the manipulator according to the first embodiment of the present invention is inserted.
Figure 7B:
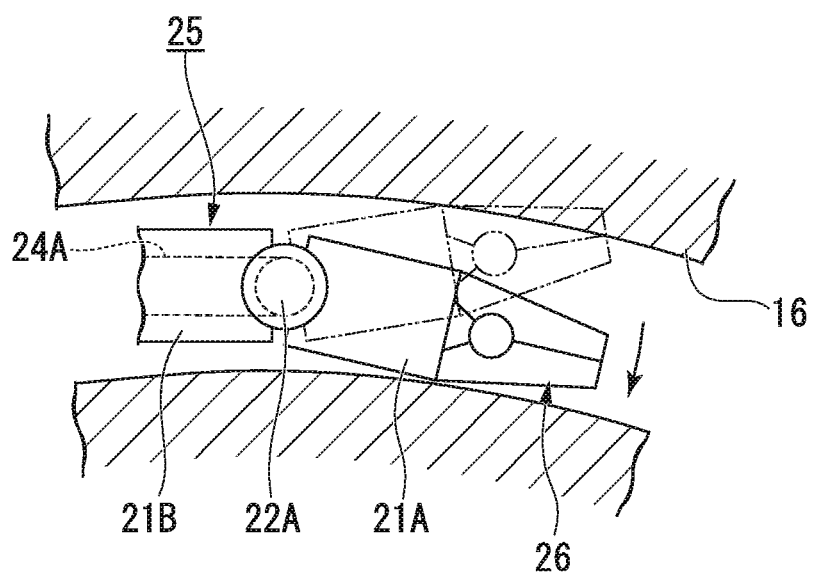
FIG. 7B is a diagram showing operations when the manipulator according to the first embodiment of the present invention is inserted.

FIG. 5 is a flowchart showing the flow of a manipulator control method according to the first embodiment of the present invention. FIG. 6 is a control block diagram of the manipulator according to the first embodiment of the present invention. FIGS. 7A and 7B are diagrams showing operations when the manipulator according to the first embodiment of the present invention is inserted. FIGS. 8A, 8B, 8C, and 8D are schematic graphs showing an example of correction for interference prevention in the manipulator control method according to the first embodiment of the present invention. In FIGS. 8A, 8B, 8C, and 8D, the horizontal axis indicates time and the vertical axis indicates an operation command value or a value corresponding to the operation command value. FIGS. 9A and 9B are schematic graphs showing an example of a manipulation command value and tension in the manipulator control method according to the first embodiment of the present invention. In FIGS. 9A and 9B, the horizontal axis indicates time and the vertical axis indicates an operation command value in FIG. 9A and tension in FIG. 9B.

When treatments are performed using the medical device 20 of the manipulator system 1, first, a distal end portion of the medical device 20 is inserted into the body of the patient P using the sheath tube 11 of the treatment endoscope device 10 and is guided to the vicinity of a treatment target portion.

In this case, since the sheath tube 11 is generally bent following an insertion path inside the body, the treatment tool channel 16 inside the sheath tube 11 is also bent.

When the medical device 20 is inserted into such a treatment tool channel 16, it is necessary to insert the medical device 20 while bending the distal bending portion 25 following a bent state of the treatment tool channel 16.

In the medical device 20 according to the present embodiment, it is possible to easily insert the medical device 20 by executing the manipulator control method according to the present embodiment to be described below.

The manipulator control method according to the present embodiment includes executing steps S1 to S11 shown in FIG. 5 according to the flow shown in FIG. 5.

In step S1, the distal end of the medical device 20 which is a manipulator is disposed in the supply opening 16a.

In this step, the operator Op inserts at least a portion of the distal bending portion 25 into the supply opening 16a from the side close to the grasping portion 26 in a closed state. In this case, the tubular portion 23 on the rear end side is supported by the hand of the operator Op, an appropriate jig, or the like.

In this way, step S1 ends.

Subsequently, step S2 is performed. In this step, the insertion control mode is selected by the manipulating portion 32.

The operator Op operates the mode switch 32a of the manipulating portion 32 to select the insertion control mode.

When the insertion control mode is selected, manipulation of the bending manipulation button 32b and manipulation of the manipulation lever 32c are disabled, and the respective joints 22 of the distal bending portion 25 start operating according to the operation command value transmitted from the control unit 36.

The operation command value causes periodic reciprocating rotation with a predetermined amplitude. However, this operation command value is sequentially corrected by the control unit 36 when external force is applied to the distal bending portion 25, which will be described later.

In this way, step S2 ends.

Subsequently, step S3 is performed. In this step, the operator Op starts inserting the medical device 20.

The operator Op starts inserting the medical device 20 by allowing the distal bending portion 25 and the tubular portion 23 to advance.

In this way, step S3 ends.

When step S3 ends, the control unit 36 executes steps S4 to S11 to be described later. In this case, although the joints 22A and 22B are automatically controlled simultaneously, since the respective control operations are the same, the control operation of the joint 22A will be mainly described.

First, an outline of the control by the control unit 36 will be described with reference to FIG. 6 which is a control block diagram for when the joint 22A is controlled by the control unit 36.

As shown in FIG. 6, the driving motor 34A is driven by the motor controller 100A when an encoder output θ1 of the driving motor 34A detected by the encoder 34Ab is fed back using an operation command value θref transmitted from the operation command value setting portion 101A as a target value.

When the driving motor 34A is driven, the driving pulley 33A (not shown) of the driving motor 34A is rotated. In this way, the driving wire 24A (not shown) wound around the driving pulley 33A is pulled, a pulley (not shown) around which the driving wire 24A is wound rotates, and the joint 22A is driven.

Due to this, a transmission system 37A including the driving pulley 33A, the driving wire 24A, the sheath 27, the tubular portion 23, the pulley of the joint 22A, and the like is interposed between the driving motor 34A and the joint 22A.

In the present embodiment, the tension detection portion 35A is provided in the driving wire 24A in the proximal housing 31, and the tension generated by the driving wire 24A can be detected.

The tension generated in the driving wire 24A mainly indicates the magnitude of a load acting on the joint 22A.

Although such a load is, to some extent, generated due to the frictional force received by the driving wire 24A and the inertia or the like of the distal bending portion 25 located closer to the front side than the joint 22A, the load tends to increase when the movement of the joint 22A is restricted by external force.

For example, when the distal bending portion 25 is inserted into the treatment tool channel 16, unless the joint 22A is appropriately rotated in relation to the amount of bend of the treatment tool channel 16, the shaft-shaped portion 21A, the grasping portion 26, and the like (hereinafter referred to as the shaft-shaped portion 21A and the like) located closer to the distal end than the joint 22A come into contact with an inner wall of the treatment tool channel 16 and receive external force from the inner wall of the treatment tool channel 16. Due to this, the tension generated in the driving wire 24A increases remarkably.

Therefore, by performing a test or the like in advance, it is possible to estimate whether the shaft-shaped portion 21A and the like are in contact with the treatment tool channel 16 based on the magnitude of the tension of the driving wire 24A.

In the present embodiment, control is performed to reduce the rotation amount by periodically rotating the joint 22A while detecting the tension of the driving wire 24A such that the tension decreases when the tension increases to some extent. When such control is performed, it is possible to create a state in which the shaft-shaped portion 21A and the like are spaced from the treatment tool channel 16, or a state in which the shaft-shaped portion 21A and the like are in contact with the treatment tool channel 16 with low pressure therebetween.

For example, when the distal end of the distal bending portion 25 reaches the treatment tool channel 16 which is bent in a certain direction, the joint 22A rotates periodically.

For example, as shown in FIG. 7A, when the joint 22A rotates in a direction opposite to the bending direction of the treatment tool channel 16, the shaft-shaped portion 21A and the like come into contact with the inner wall of the treatment tool channel 16. Thus, the joint 22A cannot rotate and the tension of the driving wire 24A increases.

On the other hand, as shown in FIG. 7B, when the joint 22A rotates in the same direction as the bending direction of the treatment tool channel 16, the shaft-shaped portion 21A and the like do not easily come into contact with the inner wall of the treatment tool channel 16. Thus, even when the shaft-shaped portion 21A and the like come into contact with the inner wall, the tension of the driving wire 24A does not increase too much.

Thus, in the distal bending portion 25, when the driving of the joints 22 is controlled such that the tension generated in the driving wires 24 becomes within a certain range, the distal bending portion 25 automatically bends repeatedly within the range of the gap between the treatment tool channel 16 and the distal bending portion 25. Due to this, the average bending state of the distal bending portion 25 follows the bend of the treatment tool channel 16.

As a result, even when the amount of bend of the treatment tool channel 16 changes, the insertion load does not increase and the medical device 20 can be easily inserted into the treatment tool channel 16.

Steps S4 to S11 are specific examples of such control.

As shown in FIG. 5, in step S4, an initial value θ(t) of an operation command value in the insertion control mode is set. For example, as schematically shown by curve 200 in FIG. 8A, a sine function having an amplitude a and a cycle τ can be employed as θ(t). That is, θ(t) can be expressed by Equation (1) below.

$$\theta(t) = a\sin(2\pi t/\tau) + \beta(t) \qquad (1)$$

Here, β(t) is a parameter used for the control to be described later, and the initial value is β(t)=0. The amplitude a may be a value that is slightly smaller than half the maximum gap between the distal bending portion 25 and the treatment tool channel 16. The cycle τ may be determined based on an insertion speed and is set to approximately 4 sec, for example.

In this way, step S4 ends.

Subsequently, step S5 is performed. In this step, the operation command value setting portion 101A acquires an encoder output θ2 from the encoder 34Bb of the joint 22B and corrects θ(t) based on an interference prevention compensation amount −θi corresponding to the encoder output θ2.

The joints 22A and 22B can be driven independently, and the bending state of the distal bending portion 25 changes with driving of the respective joints. Since this bending state causes a change in the driving loads of the driving wires 24A and 24B depending on a device condition of the distal bending portion 25, the operation command value of the driving motor 34A (34B) may sometimes have an influence on the rotation amount of the joint 22B (22A). For example, although a path length of the driving wire 24 is approximately constant in the sheath 27, since the driving wire 24 protrudes from the sheath 27 near the joint 22, the path length is influenced by the bending state of the joint 22.

Due to this, even when the joint 22B on the rear end side is rotating in a certain direction, the joint 22A may sometimes move by being influenced by the rotation. Moreover, the reverse is also possible.

Since the influence of the movement of another joint is unique to the device condition, the influence can be examined by performing a test or the like in advance.

Figure 8A:
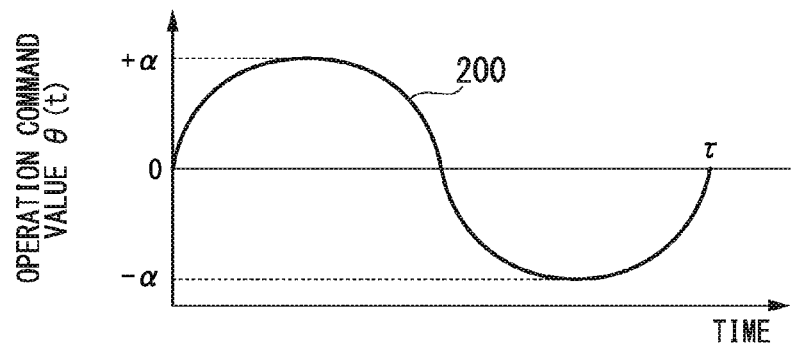
FIG. 8A is a schematic graph showing an example of correction for interference prevention in the manipulator control method according to the first embodiment of the present invention.
Figure 8B:
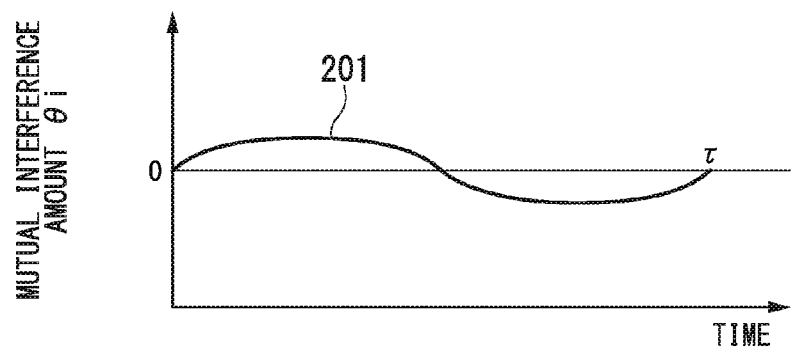
FIG. 8B is a schematic graph showing an example of correction for interference prevention in the manipulator control method according to the first embodiment of the present invention.
Figure 8C:
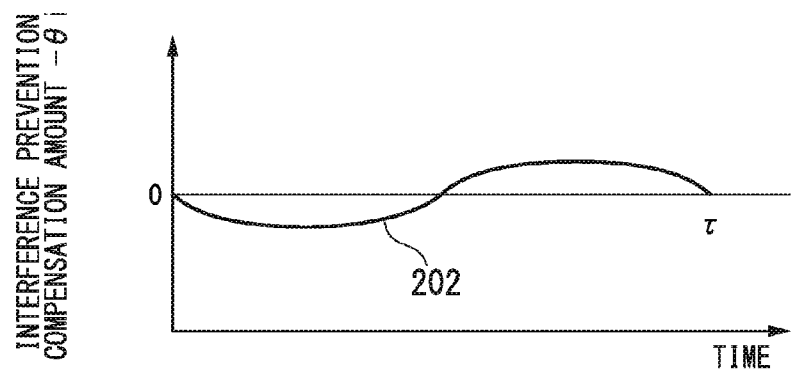
FIG. 8C is a schematic graph showing an example of correction for interference prevention in the manipulator control method according to the first embodiment of the present invention.
Figure 9A:
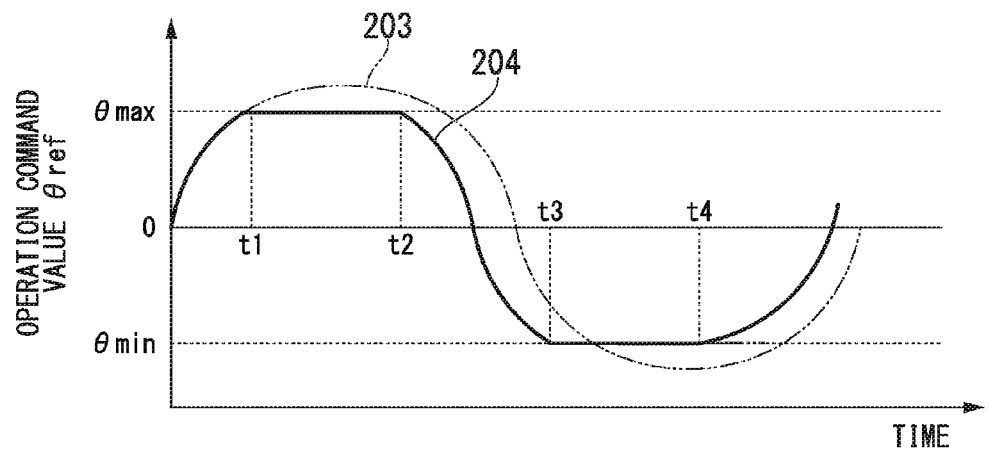
FIG. 9A is a schematic graph showing an example of a manipulation command value in the manipulator control method according to the first embodiment of the present invention.
Figure 9B:
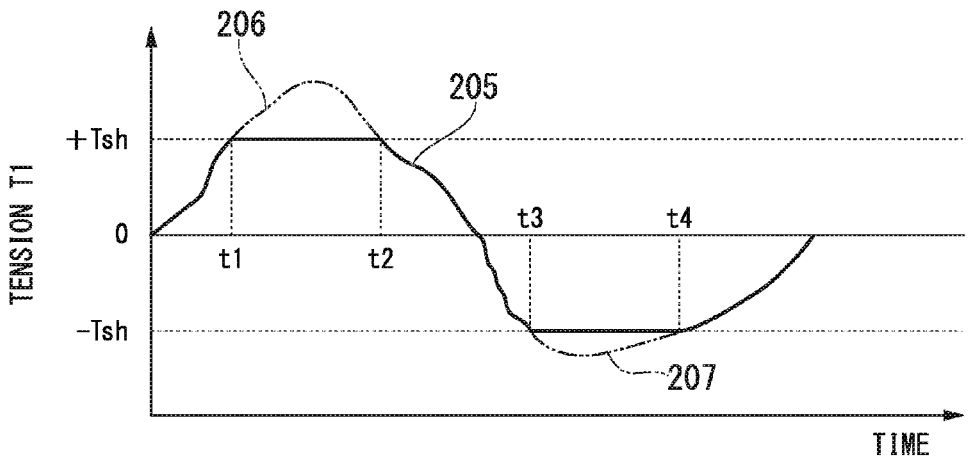
FIG. 9B is a schematic graph showing an example of tension in the manipulator control method according to the first embodiment of the present invention.

For example, a mutual interference amount θi schematically shown by curve 201 in FIG. 8B is an operation command value which is converted from an operation amount of the joint 22A which moves due to an influence of the joint 22B driven with the operation command value θ(t) defined in Expression (1).

It is preferable to remove such a mutual interference amount θi since the amount is a kind of disturbance to a control system of the joint 22A.

In this step, feedforwnvard control is performed to correct the magnitude of θ(t) using the mutual interference amount θi which is acquired in advance and stored in a data table or the like, for example.

Figure 8D:
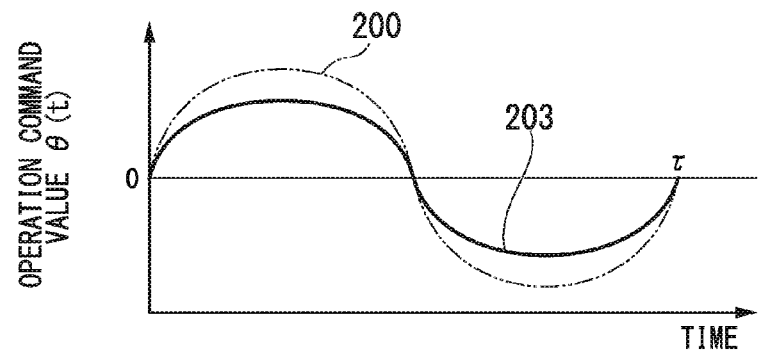
FIG. 8D is a schematic graph showing an example of correction for interference prevention in the manipulator control method according to the first embodiment of the present invention.

Thus, the operation command value setting portion 101A calculates an interference prevention compensation value −θi (see curve 202 in FIG. 8C) obtained by inverting the sign of the mutual interference amount θi determined by the encoder output θ2 and adds the same to θ(t) (see curve 203 in FIG. 8D).

In this way, step S5 ends.

Subsequently, step S6 is performed. In this step, the tension detection portion 35A acquires tension T1 generated in the driving wire 24A.

Subsequently, step S7 is performed. In this step, it is determined whether an absolute value of the tension T1 is equal to or larger than a predetermined threshold Tsh (Tsh>0).

The threshold Tsh is set based on tension generated when the shaft-shaped portion 21A and the like come in contact with the treatment tool channel 16.

When |T1| is equal to or larger than the threshold Tsh, since it is highly likely that the shaft-shaped portion 21A and the like are in contact with the treatment tool channel 16, the flow proceeds to step S8.

When |T1| is smaller than the threshold Tsh, since it is highly likely that the shaft-shaped portion 21A and the like are not in contact with the treatment tool channel 16, the flow proceeds to step S9.

In step S8, θ(t) is corrected such that |T1| can be controlled using the threshold Tsh as a target value.

Specifically, the operation command value setting portion 101A corrects θ(t) such that the tension T1 approaches the threshold Tsh according to a difference between the tension T1 and the threshold Tsh.

In the present embodiment, the amount of β(t) in Equation (1) is changed based on the difference between T1 and Tsh as an example.

As shown in FIG. 6, such control in this step corresponds to performing feedback control on the driving motor 34A using the tension T1 of the transmission system 37A as a detection output.

In this way, step S8 ends.

In step S9, the operation command value θ(t) which is corrected in step S5 and, in some cases, step S8 is transmitted to the motor controller 100A as θref.

Subsequently, step S10 is performed. In this step, the motor controller 100A drives the driving motor 34A by performing feedback control on the encoder output θ1 using the operation command value θref as a target value.

When a control signal based on the difference between the operation command value θref and the encoder output θ1 is transmitted from the motor controller 100A to the driving motor 34A, the driving motor 34A is driven.

In this way, step S10 ends.

Subsequently step S11 is performed. In this step, the operation command value setting portion 101A determines whether the insertion control mode has ended.

In this step, the operation command value setting portion 101A examines a setting state of a control mode based on a mode signal M transmitted from the mode switch 32a of the joint manipulating portion 32M.

When the control mode is set to the insertion control mode, the flow proceeds to step S4 and steps S4 to S11 are repeated.

When the control mode is set to the operation control mode, the insertion control mode ends.

In this way, when the control mode is the insertion control mode, the operation of the driving motor 34A is automatically controlled by the control unit 36.

FIGS. 9A and 9B schematically show an example of the operation command value θref and the tension T1 in the insertion control mode. The period between t1 and t2 and between t3 and t4 is a period in which the shaft-shaped portion 21A and the like are in contact with the treatment tool channel 16.

For example, as shown by curve 205 in FIG. 9B, when the tension T1 is about to exceed Tsh at time t1, θref is set to a constant value θmax by the operation command value setting portion 101A as shown in FIG. 9A.

Due to this, the rotation position of the joint 22A is fixed, bending of the shaft-shaped portion 21A and the like in relation to the shaft-shaped portion 21B become constant, and a state in which the shaft-shaped portion 21A and the like are bent following the bend of the treatment tool channel 16 is created. Therefore, as shown in FIG. 9B, the external force from the treatment tool channel 16 does not increase and T1=Tsh.

For example, when θref changes along the curve 203 in FIG. 9A, the magnitude of the tension T1 increases as shown by curve 206 in FIG. 9B. However, in the control method according to the present embodiment, the magnitude of the tension T1 does not increase.

At time t2, since the joint 22A advances into the treatment tool channel 16 having a different bent shape, the shaft-shaped portion 21A and the like are completely spaced from the treatment tool channel 16, and the magnitude of the tension T1 starts decreasing (see FIG. 9B). Due to this, θref returns to change in a sinusoidal form (see FIG. 9A).

Similarly, in the period between t3 and t4, θref is set to a constant value θmin and T1=−Tsh. Moreover, in a period after t4, θref returns to change in a sinusoidal form and the magnitude of the tension T1 decreases.

In the insertion control mode according to the present embodiment, the driving amount of the driving wire 24A by the driving motor 34A is controlled such that the tension which is a load amount is ±Tsh which is a predetermined target control range.

Since such an operation is performed similarly on the joint 22B, the entire distal bending portion 25 advances inside the treatment tool channel 16 while bending itself. When the distal bending portion 25 comes into contact with the treatment tool channel 16, the amount of bending of the distal bending portion 25 is automatically controlled to change to an amount of bending corresponding to the bend of the treatment tool channel 16.

In this manner, after the distal bending portion 25 passes through the treatment tool channel 16, the operator Op manipulates the mode switch 32a to switch the mode signal M from the insertion control mode to the operation control mode.

When mode switching is detected in step S11, the insertion control mode ends and there is a transition to the operation control mode.

In this case, since the joints 22 are under the control of the control unit 36, the last bending state in the insertion control mode is maintained and unexpected movement does not occur.

In the operation control mode, manipulation of the bending manipulation button 32b of the joint manipulating portion 32M and the manipulation lever 32c of the grasping manipulation portion 32N is enabled.

Due to this, the operator Op can move the distal bending portion 25 to the vicinity of a treatment site which is an application site and perform a necessary treatment operation while observing an image or the like which is captured by the imaging mechanism 13 and displayed on the display unit 4, for example.

According to the manipulator control method according to the present embodiment, even when the amount of bend of the treatment tool channel 16 changes, the distal bending portion 25 is automatically bent and the external force received from the treatment tool channel 16 is reduced. Due to this, for example, the operator Op can easily insert the medical device 20 without manipulating the distal bending portion 25 to correspond to the bend of the treatment tool channel 16.

Moreover, when the external force acting on the distal bending portion 25 increases, since the distal bending portion 25 is driven such that the external force is automatically relieved, the driving motors 34 do not need to have backdrivability. Due to this, since it is not necessary to add a configuration having back-drivability to the driving motors 34, it is possible to simplify the configuration.

[First Modification]

Next, a manipulator according to a modification (first modification) of the present embodiment will be described.

Figure 10:
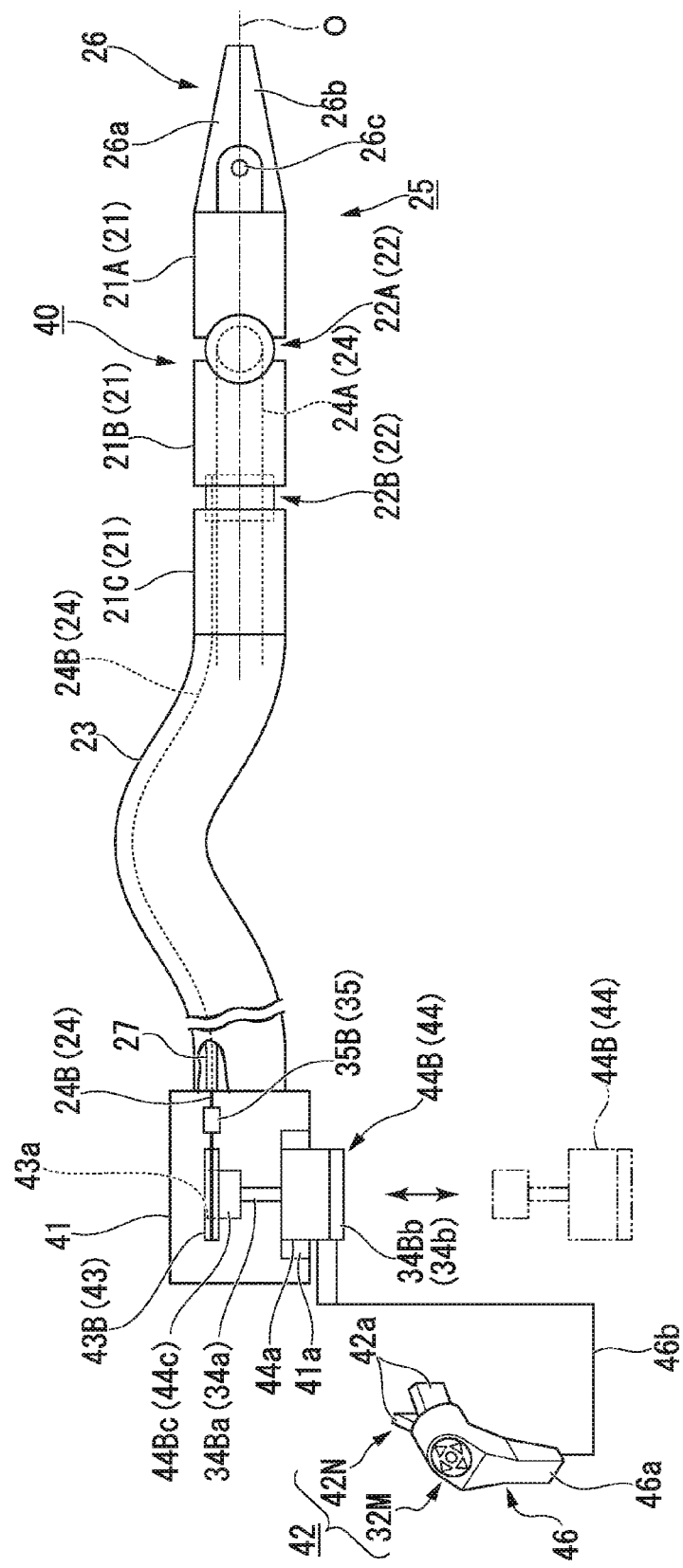
FIG. 10 is a schematic diagram showing a configuration of a manipulator according to a modification (first modification) of the first embodiment of the present invention.

FIG. 10 is a schematic diagram showing a configuration of a manipulator according to a modification (first modification) of the first embodiment of the present invention.

As shown in FIG. 10, a medical device 40 (a manipulator) according to this modification includes a proximal housing 41, a driving pulley 43, a driving motor 44 (a driving portion), and a manipulating portion 42 instead of the proximal housing 31, the driving pulley 33, the driving motor 34, and the manipulating portion 32 according to the first embodiment.

The driving pulley 43 and the driving motor 44 include driving pulleys 43A and 43B and driving motors 44A and 44B corresponding to the joints 22A and 22B similarly to the driving pulley 33 and the driving motor 34. However, the driving pulley 43A and the driving motor 44A are not shown in FIG. 10. The usage of the letters A and B is similar to the first embodiment.

The medical device 40 can be used together with the manipulator system 1 instead of the medical device 20 of the first embodiment (see FIG. 1).

Hereinafter, the difference from the first embodiment will be mainly described.

The proximal housing 41 is a device portion which is rotatably fixed to the driving pulley 43 inside the proximal housing 41 and to which the driving motors 44 are detachably attached. The proximal housing 41 is connected to the proximal end of the tubular portion 23. Due to this, the proximal housing 41 has an attachment/detachment portion 41a provided at the same axial position as the driving pulley 43 to attach and detach the driving motor 44.

The driving wire 24 is wound around the outer circumference of the driving pulley 43 similarly to the driving pulley 33, and a connecting hole 43a that detachably connects the driving motor 44 is provided at a central portion thereof.

The driving motor 44 has the same configuration as the driving motor 34 of the first embodiment except that the driving motor 44 includes a connecting portion 44a that is detachably connected to an attachment/detachment portion 41a of the proximal housing 41 and a connecting shaft 44c provided at a distal end of the output shaft 34a to be detachably connected to the connecting hole 43a of the driving pulley 43.

The configuration of the connecting portion 44a is not particularly limited as long as the connecting portion 44a can be fitted to the attachment/detachment portion 41a during attachment to fix the position of the driving motor 44 in relation to the proximal housing 41, and a mount or the like having an appropriate concave/convex fitting portion can be employed.

The connecting shaft 44c has an appropriate concave/convex structure that is fitted to the connecting hole 43a of the driving pulley 43 to be able to advance and retract in a direction along the output shaft 34a to engage with the connecting hole 43a around the output shaft 34a.

In the manipulating portion 42, the same joint manipulating portion 32M as that of the first embodiment and a grasping manipulation portion 42N for manipulating the grasping portion 26 are provided on the surface of a manipulating body 46 having a grip portion 46a that the operator Op can grasp.

Although not shown in FIG. 10, the same control unit 36 (see FIG. 4) as that of the first embodiment is provided inside the manipulating body 46.

The control unit 36 is communicably connected to the driving motor 44 and the encoder 34b by a wire cable 46b that extends outward from the manipulating body 46.

The grasping manipulation portion 42N of this modification employs a configuration in which a manipulation for an opening/closing amount of the grasping portion 26 is input by the operator Op changing an angle between a pair of knobs 42a.

The medical device 40 of this modification has the same configuration as the medical device 20 except that the driving motor 44 and the manipulating portion 42 connected thereto are provided to be detachably attached to the proximal housing 41 and the grasping manipulation portion 42N inputs a manipulation for the grasping portion 26.

Due to this, in a state in which the driving motor 44 and the manipulating portion 42 are attached to the proximal housing 41, since the same manipulator control method of the first embodiment can be executed, the same advantage of the first embodiment is obtained.

According to the medical device 40, the driving motor 44 and the manipulating portion 42 can be removed from the proximal housing 41 and be attached to another proximal housing 41.

As described above, since the driving motor 44 and the manipulating portion 42 can be detachably attached to the proximal housing 41, the driving motor 44 and the manipulating portion 42 can be detached when abandoning and sterilizing the distal bending portion 25 and the tubular portion 23 which have been used up.

The removed driving motor 44 and manipulating portion 42 can be reused by attaching the same to the proximal housing 41 of a new medical device 40 or the proximal housing 41 of a sterilized medical device 40.

[Second Embodiment]

Next, a manipulator according to a second embodiment of the present invention will be described.

Figure 11:
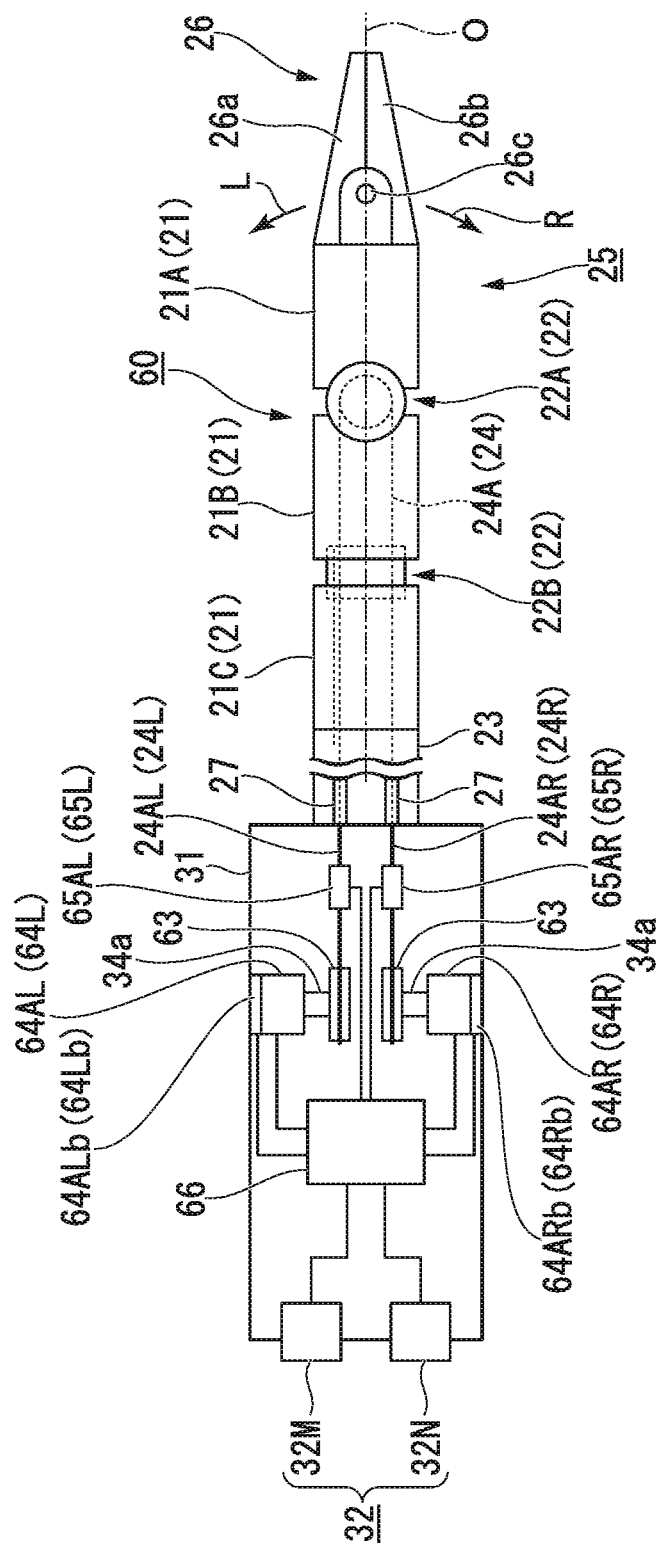
FIG. 11 is a schematic diagram showing a configuration of a manipulator according to a second embodiment of the present invention.
Figure 12:
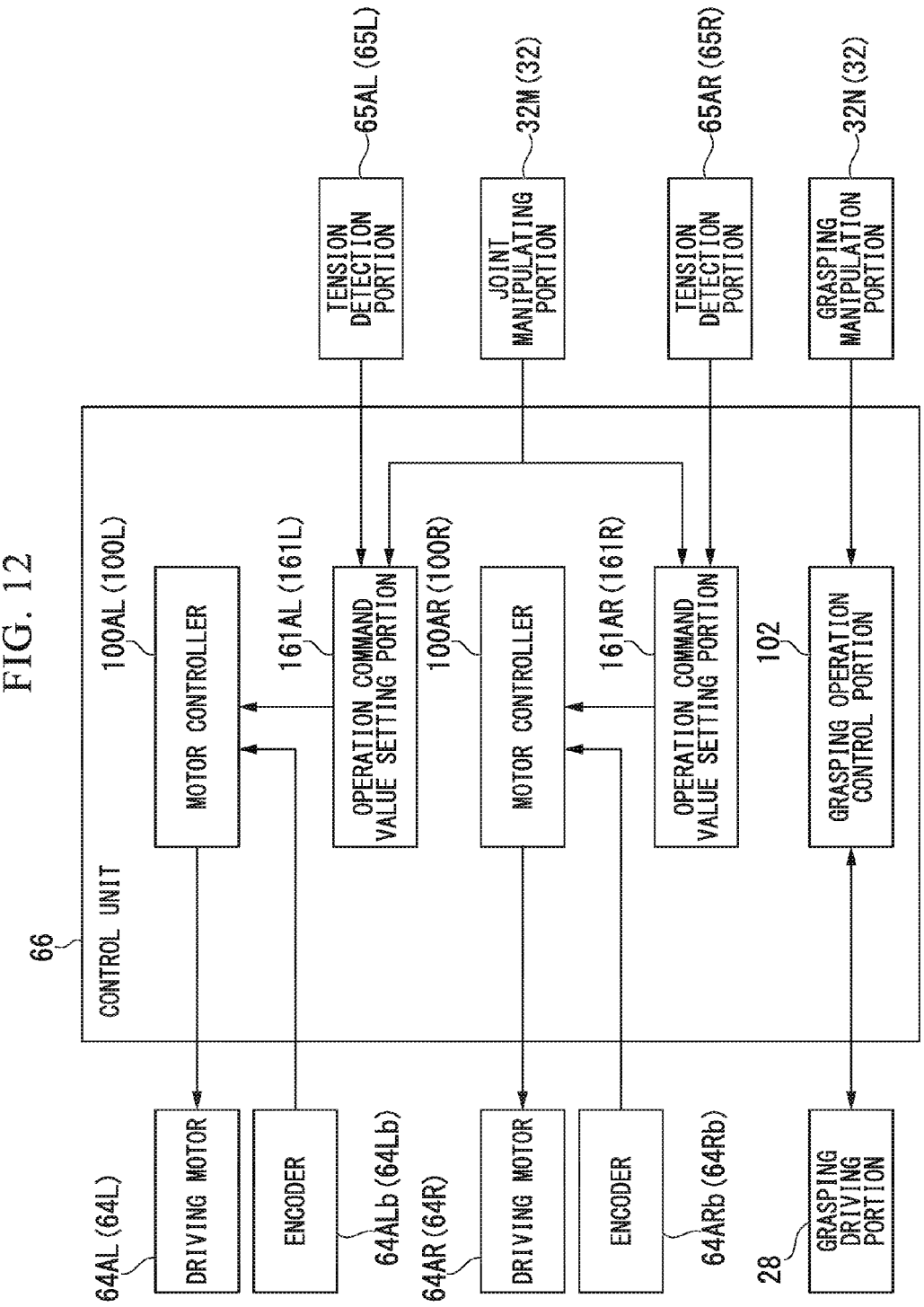
FIG. 12 is a functional block diagram showing a functional configuration of a main portion of a control unit of the manipulator according to the second embodiment of the present invention.

FIG. 11 is a schematic diagram showing a configuration of a manipulator according to a second embodiment of the present invention. FIG. 12 is a functional block diagram showing a functional configuration of a main portion of a control unit of the manipulator according to the second embodiment of the present invention.

As shown in FIG. 11, a medical device 60 (a manipulator) according to the present embodiment includes a driving motor 64L (a first driving portion or a driving portion), a driving motor 64R (a second driving portion or a driving portion), a tension detection portion 65L (a first detection portion or a load amount detection portion), a tension detection portion 65R (a second detection portion or a load amount detection portion), and a control unit 66 (an operation control portion) instead of the driving motor 34, the tension detection portion 35, and the control unit 36 according to the first embodiment.

The driving motors 64L and 64R and the tension detection portions 65L and 65R have driving motors 64AL and 64AR and 64BL and 64BR and tension detection portions 65AL and 65AR and 65BL and 65BR to correspond to the joints 22A and 22B. However, in FIG. 11, the driving motors 64BL and 64BR and the tension detection portions 65BL and 65BR having the same configurations as the driving motors 64AL and 64AR and the tension detection portions 65AL and 65AR are not shown. The usage of the letters A and B is similar to the first embodiment.

Moreover, the proximal housing 31 and the manipulating portion 32 have the same configuration as those of the first embodiment and are depicted in a more simplified manner in FIG. 11.

The medical device 60 can be used together with the manipulator system 1 instead of the medical device 20 of the first embodiment (see FIG. 1).

Hereinafter, the difference from the first embodiment will be mainly described.

The driving motors 64L and 64R are driving portions that independently drive both ends of the driving wire 24 introduced into the proximal housing 31 based on a control signal from the control unit 66 and are communicably connected to the control unit 66.

The driving motors 64L and 64R have the same output shaft 34a as the driving motor 34 and have the same encoders 64Lb and 64Rb as the encoder 34b.

A driving pulley 63 that fixes the driving wire 24 by winding it therearound is provided at a distal end of each of the output shafts 34a of the driving motors 64L and 64R.

The tension detection portions 65L and 65R are configured to detect the tension generated in a first wire portion 24L (a first transmission portion) which is one end of the driving wire 24 introduced into the proximal housing 31 and the tension generated in a second wire portion 24R (a second transmission portion) which is the other end and are communicably connected to the control unit 66.

The tension detection portions 65L and 65R may employ the same configuration as the tension detection portion 35 of the first embodiment.

As shown in FIG. 12, the control unit 66 includes motor controllers 100AL and 100AR and operation command value setting portions 161AL and 161AR instead of the motor controller 100A and the operation command value setting portion 101A of the control unit 36 according to the first embodiment.

Moreover, although not shown in FIG. 12, the control unit 66 includes motor controllers 100BL and 100BR and operation command value setting portions 161BL and 161BR instead of the motor controller 100B and the operation command value setting portion 101B of the control unit 36 according to the first embodiment. The motor controllers 100BL and 100BR and the operation command value setting portions 161BL and 161BR have the same configuration as the motor controllers 100AL and 100AR and the operation command value setting portions 161AL and 161AR.

In the following description when these members are not distinguished as to whether they are associated with the driving motor 64AL (64AR) or 64BL (64BR) or these members are collectively mentioned, the letters A and B are omitted and they are sometimes simply referred to as the motor controllers 100L and 100R and the operation command value setting portions 161L and 161R.

Specific control operations performed by the control unit 66 will be described in connection with the description of operations below.

The control unit 66 can be configured to perform correction to remove mutual interference caused by other joints similarly to the first embodiment. However, when the mutual interference is sufficiently small, correction for removing mutual interference may not be performed. In the following description, an example in which the control unit does not perform correction to remove mutual interference will be described.

Such a control unit 66 is configured as a computer including a CPU, a memory, an input and output interface, an external storage device, and the like, and an appropriate control program that realizes the above-described control function of the respective functional configurations is executed by the control unit 66.

Next, the operation of the medical device 60 of the manipulator system 1 will be described with focus on a manipulator control method according to the present embodiment.

Figure 13:
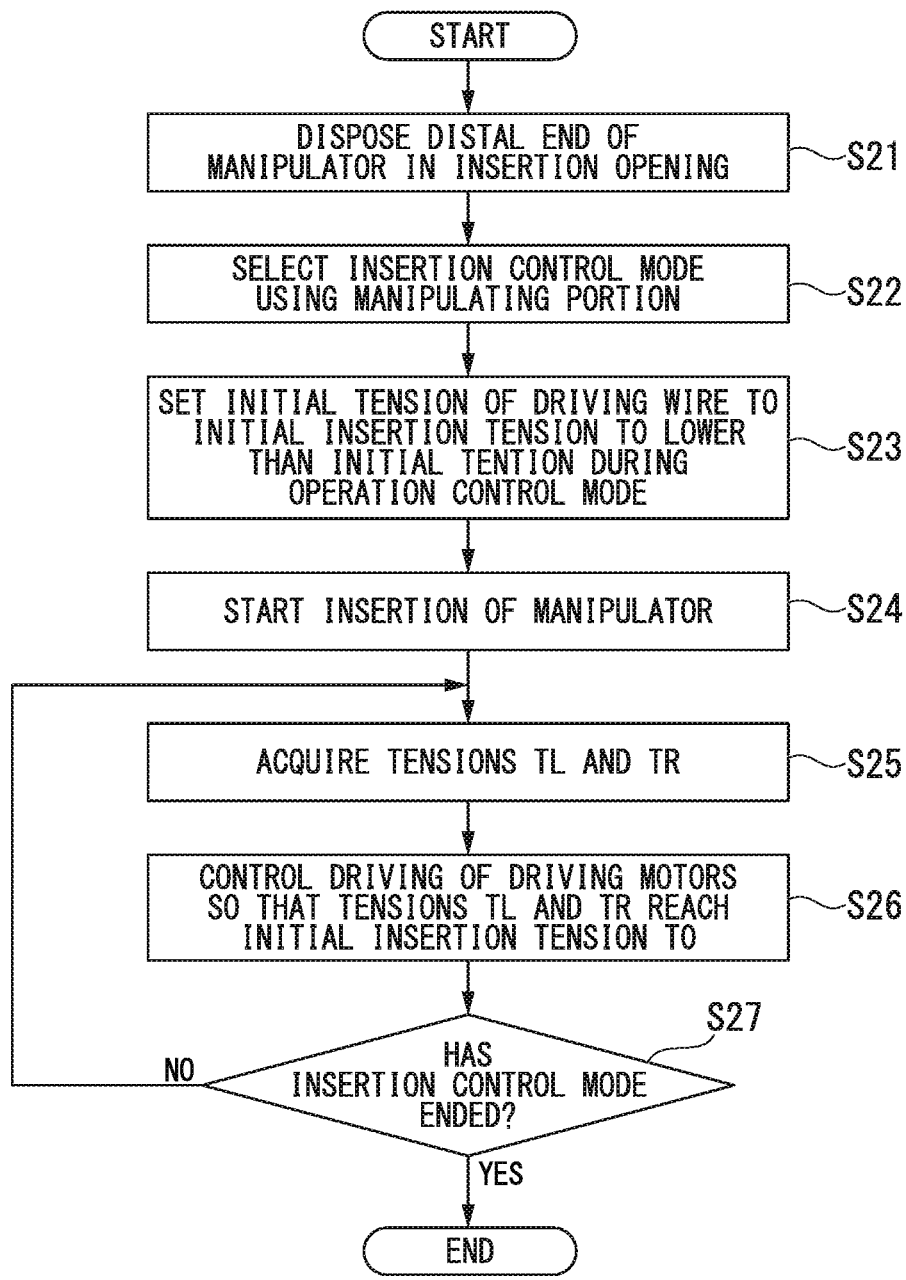
FIG. 13 is a flowchart showing the flow of the manipulator control method according to the second embodiment of the present invention.

FIG. 13 is a flowchart showing the flow of a manipulator control method according to the second embodiment of the present invention.

The manipulator control method according to the present embodiment executes steps S21 to S27 shown in FIG. 13 according to the flow shown in FIG. 13.

Step S21 is the same as step S1 of the first embodiment except that the distal end of the medical device 60 is disposed in the supply opening 16a instead of the medical device 20 of the first embodiment.

Subsequently, step S22 is performed. In this step, the insertion control mode is selected by the manipulating portion 32.

The operator Op operates the mode switch 32a of the manipulating portion 32 to select the insertion control mode.

When the insertion control mode is selected, manipulation of the bending manipulation button 32b and manipulation of the manipulation lever 32c are disabled similarly to the first embodiment.

However, in the present embodiment, the control unit 66 issues a command to the joints 22 of the distal bending portion 25 to arrange the distal bending portion 25 in a linear form.

In this way, step S22 ends.

Subsequently, step S23 is performed. In this step, initial tension of the respective driving wires 24 is set to initial insertion tension T0 lower than the initial tension during the operation control mode.

In the operation control mode, even when the distal bending portion 25 receives some degree of external force, such initial tension that the driving force of the driving motors 64L and 64R is transmitted to the joint 22 is applied to the driving wire.

The initial insertion tension T0 in this step is set to tension that can drive the joint 22 to which no external force is applied and at which driving force can be transmitted to the joint 22 even if the joint 22 receives a reaction of the pushing force of the operator Op during insertion from the treatment tool channel 16.

In the present embodiment, such initial tension T0 is realized by adjusting the rotation positions of the driving motors 64L and 64R that pull the driving wires 24 to feed the first and second wire portions 24L and 24R by an appropriate amount.

Such a feed amount is stored in advance in the operation command value setting portions 161L and 161R. Upon receiving a mode signal M for switching to the insertion control mode from the joint manipulating portion 32M, the operation command value setting portions 161L and 161R transmit an operation command value for realizing rotation corresponding to the feed amount to the motor controllers 100L and 100R.

As a result, the driving motors 64L and 64R rotate according to the control signal from the motor controllers 100L and 100R and the initial tension T0 of the first and second wire portions 24L and 24R is set.

In this way, step S23 ends.

Subsequently, step S24 is performed. In this step, the operator Op starts inserting the medical device 60.

The operator Op starts inserting the medical device 60 by allowing the distal bending portion 25 and the tubular portion 23 to advance.

In this way, step S24 ends.

When step S24 ends, the control unit 66 executes steps S25 to S27 to be described later. In this case, although the joints 22A and 22B are automatically controlled simultaneously, since the respective control operations are the same, the control operation of the joint 22A will be mainly described.

In step S25, tensions TL and TR generated in the first and second wire portions 24AL and 24AR of the driving wire 24A are acquired.

Since the distal bending portion 25 is initialized to a linear state in step S22, when the distal bending portion 25 is inserted into a bending portion of the treatment tool channel 16, the distal bending portion 25 comes in contact with the treatment tool channel 16 and receives a reaction from the treatment tool channel 16.

Due to this, the distal bending portion 25 receives external force in a direction of bending following the bent shape of the treatment tool channel 16. For example, if the treatment tool channel 16 has such a bent shape that the joint 22A bends, the load of external force is transmitted to the driving wire 24A and the tensions TL and TR of the first and second wire portions 24AL and 24AR change from the initial tension T0.

These tensions TL and TR are detected by the tension detection portions 65AL and 65AR and are transmitted to the operation command value setting portions 161AL and 161AR, respectively.

In this way, the tensions TL and TR are acquired.

In this way, step S25 ends.

Subsequently, step S26 is performed. In this step, the driving motors 64AL and 64AR are driven such that the tensions TL and TR reach the initial insertion tension T0.

Specifically, the operation command value setting portion 161AL (161AR) transmits an operation command value for performing feedback control using the initial tension T0 as a target value and using the tension TL (TR) as a detection output to the motor controller 100AL (100AR).

The motor controller 100AL (100AR) having received the operation command value transmits a control signal corresponding to the operation command value to the driving motor 64L (64R) to drive the driving motor 64L (64R).

For example, when TL>T0>TR, the distal bending portion 25 receives such external force that the shaft-shaped portion 21A rotates about the joint 22A in a direction indicated by arrow R in FIG. 11.

Due to this, in order to control the tensions TL and TR to approach the initial tension T0, driving is performed such that the first wire portion 24AL is fed and the second wire portion 24AR is pulled.

In this manner, when the tension is corrected to the initial tension T0, a state in which no external force is applied to the distal bending portion 25 and the shaft-shaped portions 21B and 21A are bent at an angle that follows the bend of the treatment tool channel 16 is created.

In this way, step S26 ends.

Subsequently, step S27 is performed. In this step, the operation command value setting portion 161AL (161AR) determines whether the insertion control mode has ended.

In this step, the operation command value setting portion 161AL (161AR) examines a setting state of a control mode based on a mode signal M transmitted from the mode switch 32a of the joint manipulating portion 32M.

When the control mode is set to the insertion control mode, the flow proceeds to step S25 and steps S25 to S27 are repeated.

When the control mode is set to the operation control mode, the insertion control mode ends.

After the distal bending portion 25 passes through the treatment tool channel 16, the operator Op manipulates the mode switch 32a to switch the mode signal M from the insertion control mode to the operation control mode similarly to the first embodiment.

When mode switching is detected in step S27, the insertion control mode ends and the control mode transitions to the operation control mode.

In the operation control mode, it is possible to perform a necessary treatment operation similarly to the first embodiment.

According to the manipulator control method of the present embodiment, when the control mode is the insertion control mode, the rotation amounts of the joints 22 are controlled such that the tension of the driving wires 24 generated according to the external force applied to the distal bending portion 25 approaches the initial insertion tension T0.

As a result, since the distal bending portion 25 is automatically controlled to the bending state following the bend of the treatment tool channel 16, even when the amount of bend of the treatment tool channel 16 changes, for example, the operator Op can easily insert the medical device 60 without manipulating the distal bending portion 25 to follow the bend of the treatment tool channel 16.

In this case, in the medical device 60, since the initial tension T0 of the driving wires 24 during insertion is set to be lower than the initial tension during the operation control mode, a change in the tension resulting from the distal bending portion 25 coming in contact with the treatment tool channel 16 is small. Due to this, since the average resistance during insertion decreases, it is possible to insert the medical device 60 with a low load.

Moreover, since the medical device 60 is driven by the driving motors 64L and 64R capable of independently driving the first and second wire portions 24L and 24R, it is possible to quickly follow a change in the respective tensions. Due to this, even when the initial tension T0 is small, it is possible to prevent the driving wire 24 from becoming out of place.

Moreover, when the external force acting on the distal bending portion 25 increases, since the distal bending portion 25 is driven such that the external force is automatically relieved, the driving motors 64L and 64R do not need to have back-drivability. Due to this, since it is not necessary to add a configuration having back-drivability to the driving motors 64L and 64R, it is possible to simplify the configuration.

[Third Embodiment]

Next, a manipulator according to a third embodiment of the present invention will be described.

Figure 14:
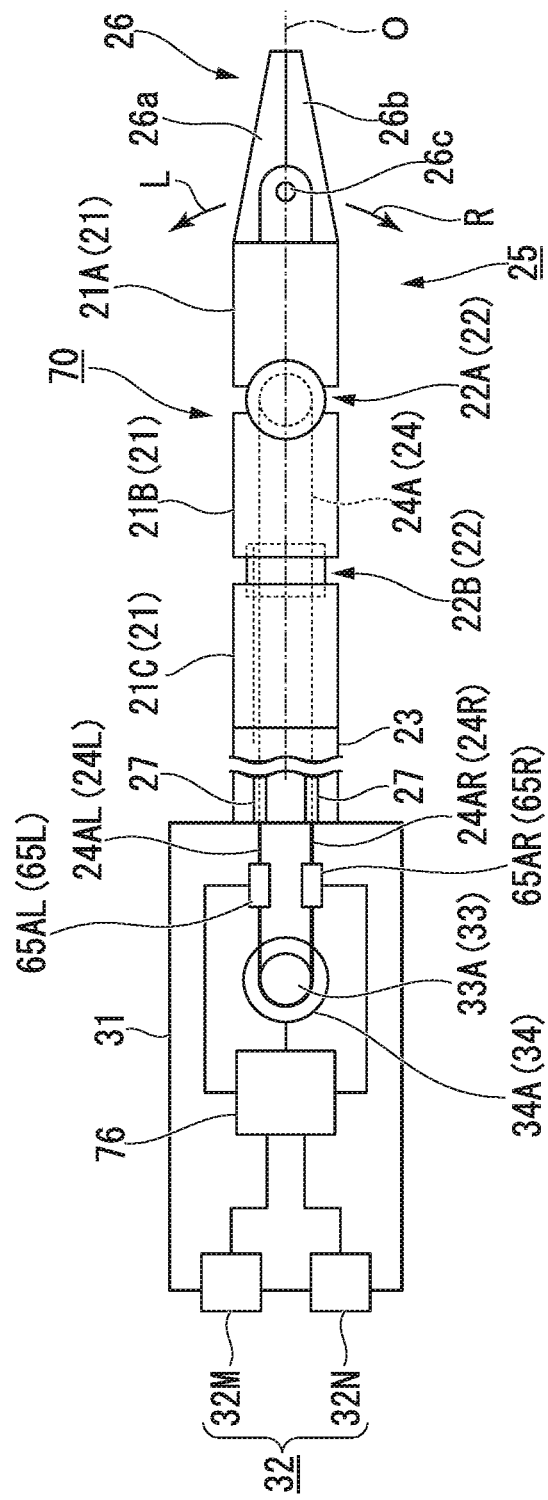
FIG. 14 is a schematic diagram showing a configuration of a manipulator according to a third embodiment of the present invention.
Figure 15:
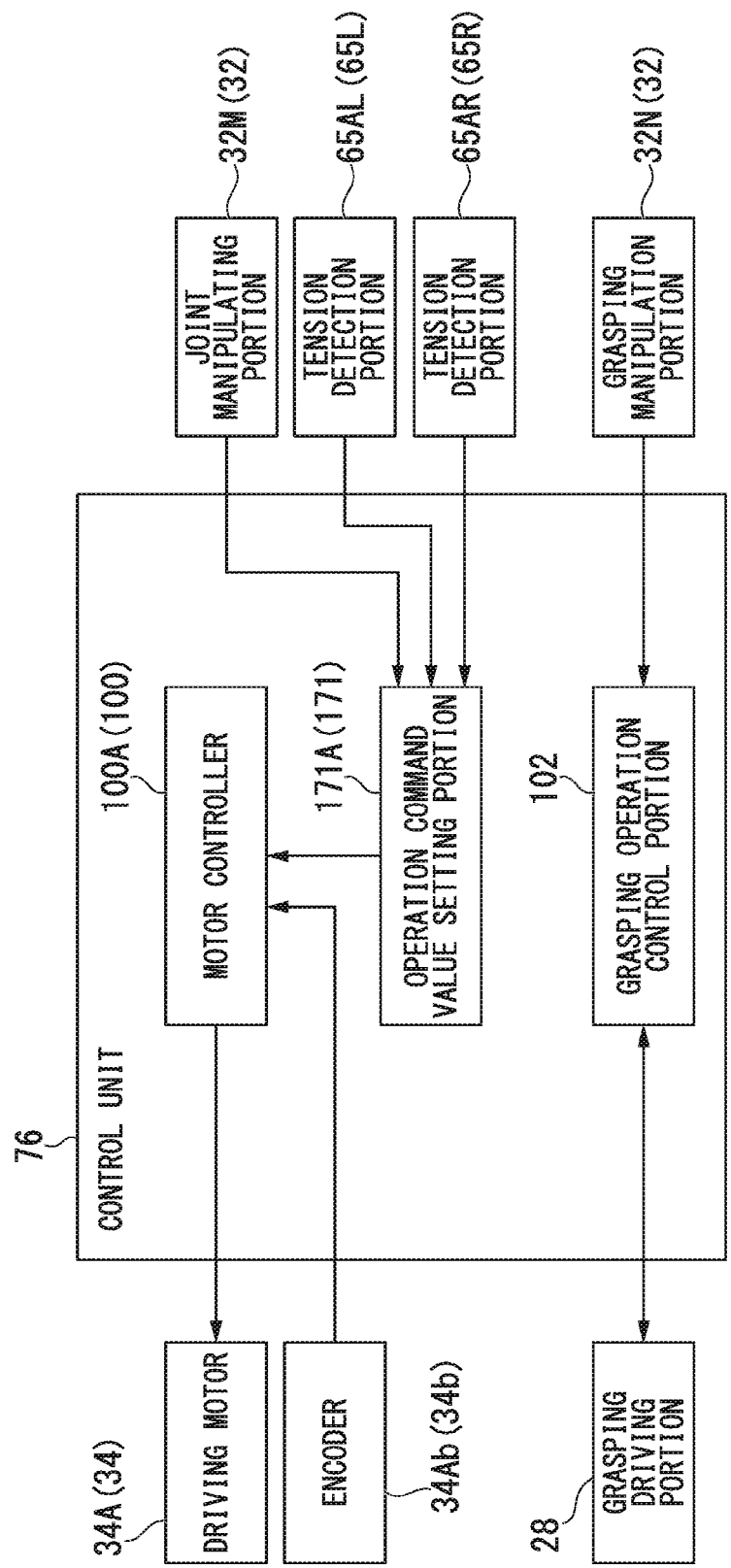
FIG. 15 is a functional block diagram showing a functional configuration of a main portion of a control unit of the manipulator according to the third embodiment of the present invention.

FIG. 14 is a schematic diagram showing a configuration of a manipulator according to a third embodiment of the present invention. FIG. 15 is a functional block diagram showing a functional configuration of a main portion of a control unit of the manipulator according to the third embodiment of the present invention.

As shown in FIG. 14, a medical device 70 (a manipulator) according to the present embodiment includes the same driving motor 34 and the same control unit 76 (the operation control portion) as those of the first embodiment instead of the driving motors 64L and 64R and the control unit 36 according to the second embodiment.

The driving motor 34 and the tension detection portions 65L and 65R have driving motors 34A and 34B and tension detection portions 65AL and 65AR and 65BL and 65BR to correspond to the joints 22A and 22B. However, the driving motor 34B and the tension detection portions 65BL and 65BR are not shown in FIG. 14. The usage of the letters A and B is the same as the first and second embodiments.

Moreover, similarly to the second embodiment, the configurations of the proximal housing 31 and the manipulating portion 32 are depicted in a more simplified manner in FIG. 14.

The medical device 70 can be used together with the manipulator system 1 instead of the medical device 20 of the first embodiment (see FIG. 1).

Hereinafter, the difference from the first embodiment will be mainly described.

As shown in FIG. 15, the control unit 76 includes a motor controller 100A and an operation command value setting portion 171A instead of the motor controllers 100AL and 100AR and the operation command value setting portions 161AL and 161AR of the control unit 66 according to the second embodiment.

Moreover, although not shown in FIG. 15, the control unit 76 includes a motor controller 100B and an operation command value setting portion 171B instead of the motor controllers 100BL and 100BR and the operation command value setting portions 161BL and 161BR of the control unit 66 according to the second embodiment.

The operation command value setting portion 171B has the same configuration as the operation command value setting portion 171A.

In the following description when these members are not distinguished as to whether they are associated with the driving motor 34A or 34B or these members are collectively mentioned, the letters A and B are omitted and they are sometimes simply referred to as the motor controller 100 and the operation command value setting portion 171.

Specific control operations performed by the control unit 76 will be described in connection with the description of operations below.

The control unit 76 can be configured to perform correction to remove mutual interference caused by other joints similarly to the first embodiment. However, when the mutual interference is sufficiently small, correction for removing mutual interference may not be performed. In the following description, an example in which the control unit does not perform correction to remove mutual interference will be described.

Such a control unit 76 is configured as a computer including a CPU, a memory, an input and output interface, an external storage device, and the like, and an appropriate control program that realizes the above-described control function of the respective functional configurations is executed by the control unit 76.

Next, the operation of the medical device 70 of the manipulator system 1 will be described with focus on a manipulator control method according to the present embodiment.

Figure 16:
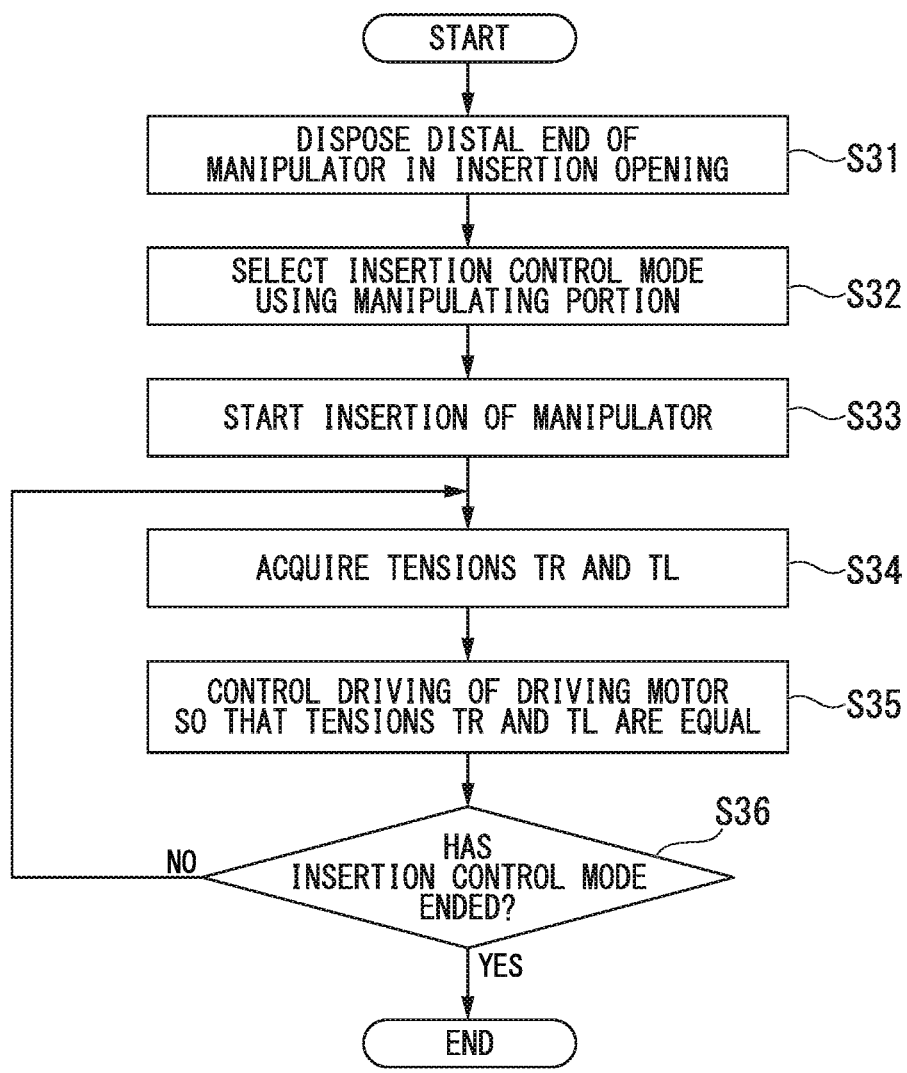
FIG. 16 is a flowchart showing the flow of the manipulator control method according to the third embodiment of the present invention.

FIG. 16 is a flowchart showing the flow of a manipulator control method according to the third embodiment of the present invention.

The manipulator control method according to the present embodiment executes steps S31 to S36 shown in FIG. 16 according to the flow shown in FIG. 16.

Steps S31, S32, and S33 are the same as steps S21, S22, and S24 of the second embodiment except that the medical device 70 is used instead of the medical device 60 of the second embodiment.

When step S33 ends, the control unit 76 performs steps S34 to S36 to be described later. In this case, although the joints 22A and 22B are automatically controlled simultaneously, since the respective control operations are the same, the control operation of the joint 22A will be mainly described.

In step S34, the tensions TL and TR generated in the first and second wire portions 24AL and 24AR of the driving wire 24A are acquired.

Since the distal bending portion 25 is initialized to a linear state in step S32, when the distal bending portion 25 is inserted into a bending portion of the treatment tool channel 16, the distal bending portion 25 comes in contact with the treatment tool channel 16 and receives a reaction from the treatment tool channel 16.

Due to this, the distal bending portion 25 receives external force in a direction of bending following the bent shape of the treatment tool channel 16. For example, if the treatment tool channel 16 has such a bent shape that the joint 22A bends, the load of external force is transmitted to the driving wire 24A and the tensions TL and TR of the first and second wire portions 24AL and 24AR change from the initial tension T0.

These tensions TL and TR are detected by the tension detection portions 65AL and 65AR and are transmitted to the operation command value setting portion 171A.

In this way, the tensions TL and TR are acquired.

In this way, step S34 ends.

Subsequently, step S35 is performed. In this step, the driving motor 34A is driven such that the tensions TL and TR are equal.

Specifically, the operation command value setting portion 171A calculates a difference between the tensions TL and TR (a tension difference) and transmits an operation command value for driving the driving motor 34A such that the difference becomes 0 to the motor controller 100A.

The motor controller 100A having received the operation command value transmits a control signal corresponding to the operation command value to the driving motor 34A to drive the driving motor 34A.

For example, when TL>TR, the distal bending portion 25 receives such external force that the shaft-shaped portion 21A rotates about the joint 22A in a direction indicated by arrow R in FIG. 14.

Due to this, in order to control the difference between the tensions TL and TR to approach 0, driving is performed such that the joint 22A rotates in the direction indicated by arrow R.

When the tensions TL and TR are equal, a state in which no external force is applied to the distal bending portion 25 and the shaft-shaped portions 21B and 21A are bent at an angle that follows the bend of the treatment tool channel 16 is created.

In this way, step S35 ends.

Subsequently, step S36 is performed. In this step, the operation command value setting portion 171A determines whether the insertion control mode has ended.

In this step, the operation command value setting portion 171A examines a setting state of a control mode based on a mode signal M transmitted from the mode switch 32a of the joint manipulating portion 32M.

When the control mode is set to the insertion control mode, the flow proceeds to step S34 and steps S34 to S36 are repeated.

When the control mode is set to the operation control mode, the insertion control mode ends.

After the distal bending portion 25 passes through the treatment tool channel 16, the operator Op manipulates the mode switch 32a to switch the mode signal M from the insertion control mode to the operation control mode similarly to the second embodiment.

When mode switching is detected in step S36, the insertion control mode ends and the control mode transitions to the operation control mode.

In the operation control mode, it is possible to perform a necessary treatment operation similarly to the second embodiment.

According to the manipulator control method of the present embodiment, when the control mode is the insertion control mode, the rotation amounts of the joints 22 are controlled such that the tensions TL and TR of the driving wires 24 generated according to the external force applied to the distal bending portion 25 are equal.

As a result, since the distal bending portion 25 is automatically controlled to the bending state following the bend of the treatment tool channel 16, even when the amount of bend of the treatment tool channel 16 changes, for example, the operator Op can easily insert the medical device 70 without manipulating the distal bending portion 25 to follow the bend of the treatment tool channel 16.

Moreover, when the external force acting on the distal bending portion 25 increases, since the distal bending portion 25 is driven such that the external force is automatically relieved, the driving motors 34 do not need to have back-drivability. Due to this, since it is not necessary to add a configuration having back-drivability to the driving motors 34, it is possible to simplify the configuration.

[Second Modification]

Next, a manipulator and a manipulator system according to a modification (second modification) of the present embodiment will be described.

Figure 17:
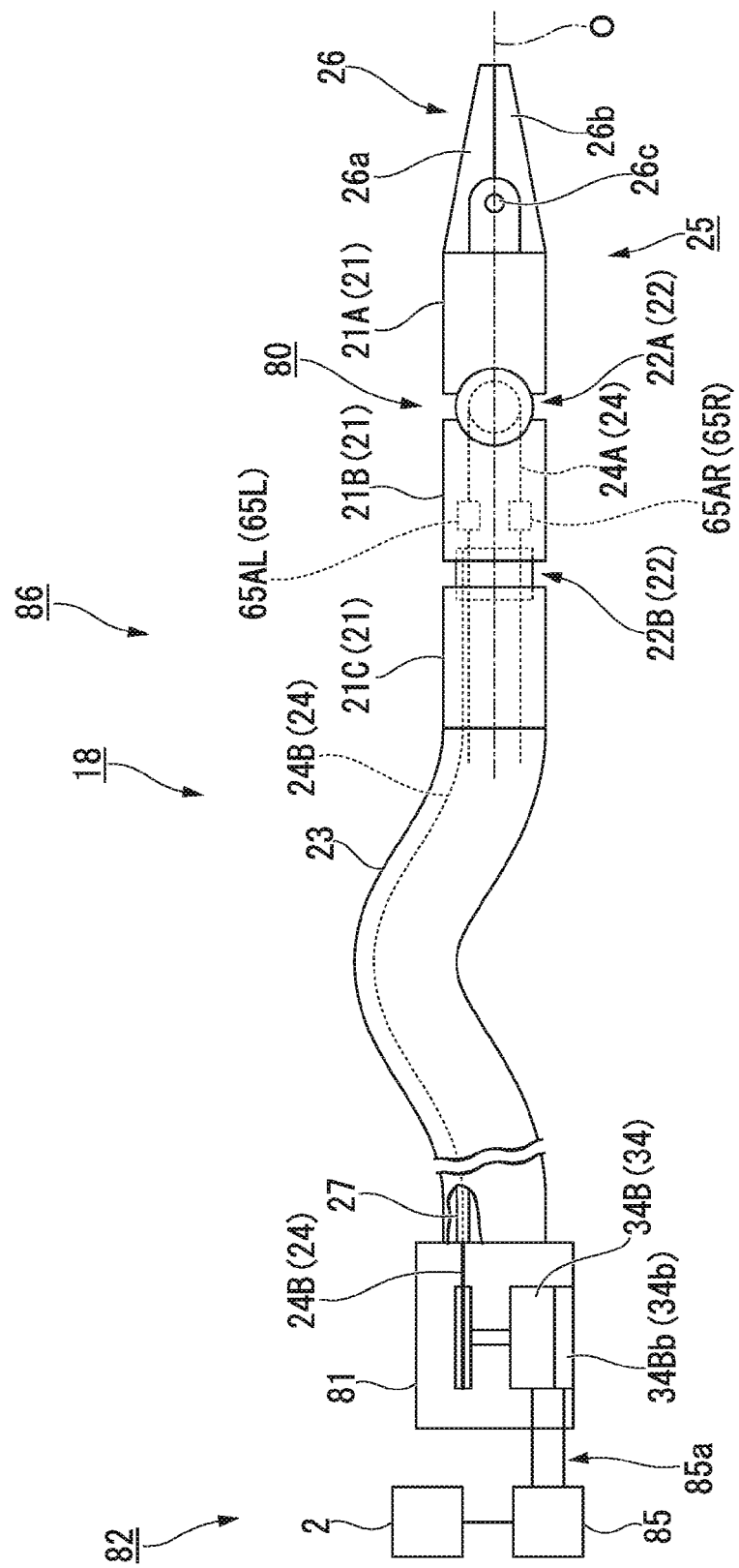
FIG. 17 is a schematic diagram showing a configuration of a main portion of a manipulator and a manipulator system according to a modification (second modification) of the third embodiment of the present invention.

FIG. 17 is a schematic diagram showing a configuration of a main portion of a manipulator and a manipulator system according to a modification (second modification) of the third embodiment of the present invention.

As shown in FIG. 17, a main portion of a manipulator system 18 of this modification includes a medical device 80 (a manipulator), a master manipulator 82, a control unit 85 (an operation control portion), and a slave manipulator 86 instead of the medical device 20, the master manipulator 2, the control unit 5, and the slave manipulator 6 of the manipulator system 1 according to the first embodiment.

In the medical device 80, the manipulating portion 32 and the control unit 36 of the first embodiment are removed, and a proximal housing 81 is included instead of the proximal housing 31. The tension detection portions 65L and 65R of the third embodiment are provided in portions of the driving wires 24 inserted into the distal bending portion 25.

The driving motor 34, the driving wire 24, and the tension detection portions 65L and 65R have the driving motors 34A and 34B, the driving wires 24A and 24B, and the tension detection portions 65AL and 65AR and 65BL and 65BR to correspond to the joints 22A and 22B similarly to the third embodiment. However, the driving motor 34A and the tension detection portions 65BL and 65BR are not shown in FIG. 17. The usage of the letters A and B is similar to the third embodiment.

Hereinafter, the difference from the first and third embodiments will be mainly described.

The proximal housing 81 is a device portion in which the driving motors 34 are disposed and which is connected to the proximal end of the tubular portion 23. The driving motors 34 and the encoders 34b are communicably connected to the control unit 85 (described later) via a wire cable 85a.

Wires (not shown) which are connected to the tension detection portions 65L and 65R provided inside the distal bending portion 25 and are inserted into wires wired inside the distal bending portion 25, the tubular portion 23, and the proximal housing 81 are also inserted into the wire cable 85a. In this way, the detection outputs of the tension detection portions 65L and 65R are transmitted to the control unit 85 to be described later.

The master manipulator 82 includes the control unit 85 instead of the control unit 5 of the master manipulator 2 according to the first embodiment.

The control unit 85 has a configuration in which the control function of the control unit 76 according to the third embodiment is added to the control function of the control unit 5.

All manipulation inputs on the control unit 85 including a manipulation input related to the operation of the medical device 80 are input using the master arm 3.

In manipulation of the master arms 3, the treatment endoscope device 10 may be manipulated using one of a pair of master arms 3 and the medical device 80 may be manipulated using the other master arm. Alternatively, a manipulation of the treatment endoscope device 10 and a manipulation of the medical device 80 may be switched by an appropriate manipulating portion.

When the medical device 80 is manipulated, a manipulating portion having the joint structure of the master arm 3 is allocated to a bending manipulation like the bending manipulation button 32b of the third embodiment, and the grasping manipulation portion of the master arm 3 is allocated to a grasping manipulation like the grasping manipulation portion 32N of the third embodiment.

Furthermore, another manipulating portion (not shown) of the master arm 3 is allocated to a mode switching operation like the mode switch 32a of the third embodiment.

Due to this configuration, the medical device 80 is a slave manipulator operated by the master arm 3 of the manipulator system 18.

That is, the slave manipulator 86 of this modification has a configuration in which the medical device 80 which is a slave manipulator is added to the slave manipulator 6 of the first embodiment.

The manipulator system 18 of this modification is a master slave system in which the medical device 80 capable of performing the same operation as the medical device 70 of the third embodiment is incorporated as one of slave manipulators.

Due to this, as long as the control mode of the medical device 80 is switched to the insertion control mode by the master arm 3, it is possible to insert the distal bending portion 25 and the tubular portion 23 of the medical device 80 into the treatment tool channel 16 in the same manner as in the third embodiment.

In the third embodiment, an example in which the medical device 70 is inserted by human hands has been described. However, the medical device may be easily manipulated by a robot since such an insertion manipulation involves simply positioning the distal end of the medical device 80 in the supply opening 16a and sending the medical device 80 in the axial direction.

For example, the medical device 80 may be inserted by the multi-joint robot 8 for insertion manipulation by providing the multi-joint robot 8 in the slave manipulator 86.

In the description of the operation of the embodiments and the modifications, an example in which the manipulator is inserted into the channel member has been described. However, the same control is performed when the manipulator which has been inserted into the channel member and has performed a treatment or the like is removed to the outside through the channel member. Therefore, it is possible to easily remove the manipulator similarly to the insertion.

Although the treatment tool channel 16 of the treatment endoscope device 10 has been described as an example of a channel member in the description of the embodiments and the modifications, the channel member is not limited to this. The channel member may be a so-called flexible overtube, for example. In this case, the inside of the overtube forms the insertion path of the manipulator.

In the description of the embodiments and the modifications, an example in which the grasping portions 26 which are grasping forceps are included as the end effector of the manipulator has been described. However, the end effector is not limited to the grasping portion 26 and an appropriate device configuration (for example, a high-frequency treatment tool, an injection needle, separating forceps, suction, or the like) may be used depending on the kind of surgery. Moreover, the end effector is not limited to a movable mechanism like the grasping portion 26. For example, an end effector which is fixed to a distal end like the observation unit 15 of the treatment endoscope device 10 may be used.

In the description of the embodiments and the modifications, an example in which the manipulator control method is a medical manipulator control method has been described. However, the present invention can be similarly applied to manipulators (for example, industrial manipulators) other than the medical manipulator.

Although an example in which the distal bending portion 25 has two joints 22A and 22B having different bending directions has been described in the description of the embodiments and the modifications, the number of joints and the degree of freedom may be set appropriately by taking the content or the like of surgery into consideration. For example, the distal bending portion 25 may have only one joint or three or more joints.

Moreover, instead of a combination of the joint and the tubular portion, a mechanism like the bending portion 11B of the sheath tube 11 may be used. That is, a plurality of joint rings and bending pieces which are the shaft-shaped portions may be connected by a rotary joint which is a bending joint.

Although an example in which the power transmission member is a wire has been described in the description of the embodiments and the modifications, the power transmission member is not limited to a wire. The power transmission member may be a cable, a flexible rod, or a combination thereof, for example.

For example, although an example in which the driving wire 24 is driven by the driving pulley 33 or the like has been described in the description of the embodiments and the modifications, the end of the driving wire 24 may be connected to a pair of racks and a pinion that drives these racks may be rotated by a driving motor.

Although an example in which the tension of the power transmission member is detected as a load amount has been described in the description of the embodiments and the modifications, the load amount is not limited to the tension. For example, in a case where the power transmission member is a rod, a stress or a strain amount generated in the rod may be used as the load amount.

Moreover, the load amount is not limited to the amount generated in the power transmission member but may be a load amount generated in the driving portion.

An example of the load amount generated in the driving portion is a driving current amount generated in the driving motor 34.

Although a case in which the joint includes a bending joint only has been described in the description of the embodiments and the modifications, the joint may include a rotary joint that rotates about the central axis of the shaft-shaped portion, for example.

For example, even when a portion bent by another bending joint follows a curved shape of the channel member, if the bending direction is different from the curving direction, the load increases. However, in this case, since the rotary joint rotates, the bending portion rotates and the bending direction of the bending portion can match the curving direction of the channel member. In this way, the load decreases and the insertion is made easy.

Although an example in which the operation command value $\theta(t)$ is corrected by changing $\beta(t)$ in Expression (1) to change an offset amount of a sine wave has been described in the description of the first embodiment, this is an example only.

For example, θ(t) may be corrected by changing the amplitude a in Expression (1).

Moreover, θ(t) is not limited to a sine function as long as it is a periodic function.

All constituent elements described above may be appropriately combined and omitted within the range of the technical scope of the present invention.

For example, correction for removing mutual interference described in the first embodiment may be applied to the control methods of the second and third embodiments.

Moreover, the correction for removing mutual interference in the first embodiment may be omitted.

Furthermore, in the third embodiment, the initial insertion tension of the driving wire 24 may be set to be lower than the initial tension during the operation control mode similarly to the second embodiment.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A manipulator control method for controlling a manipulator which includes a joint structure portion having one or more joints connected to a distal end of an insertion portion, a power transmission member inserted into the insertion portion to transmit driving force to the joint structure portion, and a driving portion that drives the power transmission member, and which is guided to an application site by being inserted into a channel member,
   wherein when the manipulator is operated in an insertion control mode used for inserting the joint structure portion into the channel member, the manipulator control method comprising:
   detecting a load amount generated in the power transmission member or the driving portion; and
   creating a bending state in which the joint structure portion follows the channel member by controlling a driving amount of the power transmission member by the driving portion such that the load amount becomes within a predetermined target control range.

2. The manipulator control method according to claim 1, wherein
   the load amount is a tension generated in the power transmission member.

3. The manipulator control method according to claim 1, wherein the manipulator control method further includes:
   detecting the load amount while bending the joint by supplying an operation command value for allowing the joint to perform a bending operation periodically to the driving portion; and
   performing control to change the operation command value such that a maximum value and a minimum value of the load amount become within the target control range.

4. The manipulator control method according to claim 3, wherein
   in a case where the joint structure portion has a plurality of the joints,
   when the operation command value is going to be supplied to a control target joint of the joint structure portion, the manipulator control method further includes:
   detecting a bending state of the other joint of the joint structure portion; and
   supplying the operation command value which involves correction for removing influence of mutual interference caused by the other joint based on the bending state of the other joint.

5. The manipulator control method according to claim 2,
   wherein the power transmission member has a first transmission portion that bends the joint in a first direction and a second transmission portion that bends the joint in a second direction opposite to the first direction,
   wherein the driving portion has a first driving portion that drives the first transmission portion and a second driving portion that drives the second transmission portion, and
   wherein the manipulator control method further includes:
   detecting tensions generated in the first and second transmission portions; and
   performing control to drive the first and second transmission portions by independently driving the first and second driving portions such that both of the tensions are equal to a predetermined initial insertion tension.

6. The manipulator control method according to claim 2,
   wherein the power transmission member has a first transmission portion that bends the joint structure portion in a first direction and a second transmission portion that bends the joint structure portion in a second direction opposite to the first direction, and
   wherein the manipulator control method further includes:
   detecting tensions generated in the first and second transmission portions to acquire information of a tension difference between these tensions; and
   performing control to drive the power transmission member to cause the tension difference to be 0.

7. The manipulator control method according to claim 5, wherein
   an initial tension of the power transmission member is set to be lower than an initial tension of the power transmission member when the manipulator is used at the application site.

8. The manipulator control method according to claim 6, wherein
   an initial tension of the power transmission member is set to be lower than an initial tension of the power transmission member when the manipulator is used at the application site.

9. A manipulator which is guided to an application site by being inserted into a channel member, comprising:
   a joint structure portion having one or more joints connected to a distal end of an insertion portion;
   a power transmission member inserted into the insertion portion to transmit driving force to the joint structure portion;
   a driving portion that is configured to drive the power transmission member;
   a load amount detection portion that is configured to detect a load amount generated in the power transmission member or the driving portion; and
   an operation control portion that is configured to control an operation of the joint structure portion,
   wherein the operation control portion sets an insertion control mode for inserting the joint structure portion into the channel member, and wherein the operation control portion controls a driving amount of the power transmission member by the driving portion such that the load amount detected by the load amount detection portion becomes within a predetermined target control range to create a bending state in which the joint structure portion follows the channel member, when the operation control portion is set to the insertion control mode.

10. The manipulator according to claim 9, wherein the load amount detection portion detects a tension generated in the power transmission member as the load amount.

11. The manipulator according to claim 9,
wherein the operation control portion detects the load amount while bending the joint by supplying an operation command value to the driving portion for allowing the joint to perform a bending operation periodically, and
wherein the operation control portion performs control to change the operation command value such that a maximum value and a minimum value of the load amount become within the target control range.

12. The manipulator according to claim 11,
wherein the joint structure portion has a plurality of joints, and
wherein the operation control portion detects a bending state of the other joint of the joint structure portion, and supplies the operation command value which involves correction for removing influence of mutual interference caused by the other joint based on the bending state of the other joint, when the operation command value is going to be supplied to a control target joint of the joint structure portion.

13. The manipulator according to claim 10,
wherein the power transmission member has a first transmission portion that bends the joint in a first direction and a second transmission portion that bends the joint in a second direction opposite to the first direction,
wherein the driving portion has a first driving portion that drives the first transmission portion and a second driving portion that drives the second transmission portion,
wherein the load amount detection portion has a first detection portion that detects the tension of the first transmission portion and a second detection portion that detects the tension of the second transmission portion, and
wherein the operation control portion performs control to drive the first and second transmission portions by independently driving the first and second driving portions such that the tensions detected by the first and second detection portions are equal to a predetermined initial insertion tension.

14. The manipulator according to claim 10,
wherein the power transmission member has a first transmission portion that bends the joint in a first direction and a second transmission portion that bends the joint in a second direction opposite to the first direction,
wherein the load amount detection portion has a first detection portion that detects the tension of the first transmission portion and a second detection portion that detects the tension of the second transmission portion, and
wherein the operation control portion acquires information on a tension difference between the tension detected by the first detection portion and the tension detected by the second detection portion; and the operation control portion performs control to drive the power transmission member to cause the tension difference to reach 0.

15. The manipulator according to claim 13, wherein an initial tension of the power transmission member is set to be lower than an initial tension of the power transmission member when the manipulator is used at the application site.

16. The manipulator according to claim 14, wherein an initial tension of the power transmission member is set to be lower than an initial tension of the power transmission member when the manipulator is used at the application site.

17. A manipulator system comprising:
the manipulator according to claim 9; and
a master manipulator configured to control the manipulator corresponding to operations on the master manipulator from an operator.

* * * * *